US009096660B2

(12) United States Patent
Trieu et al.

(10) Patent No.: US 9,096,660 B2
(45) Date of Patent: Aug. 4, 2015

(54) SPARC BINDING ANTIBODIES AND USES THEREOF

(75) Inventors: Vuong Trieu, Agoura Hills, CA (US); Xiping Liu, Temple City, CA (US); Neil Desai, Los Angeles, CA (US)

(73) Assignee: Abraxis BioScience, LLC, Los Angeles, CA (US)

( * ) Notice: Subject to any disclaimer, the term of this patent is extended or adjusted under 35 U.S.C. 154(b) by 24 days.

(21) Appl. No.: 13/643,609

(22) PCT Filed: Apr. 26, 2011

(86) PCT No.: PCT/US2011/033934
§ 371 (c)(1),
(2), (4) Date: Jan. 7, 2013

(87) PCT Pub. No.: WO2011/137114
PCT Pub. Date: Nov. 3, 2011

(65) Prior Publication Data
US 2013/0101504 A1    Apr. 25, 2013

Related U.S. Application Data

(60) Provisional application No. 61/328,172, filed on Apr. 26, 2010.

(51) Int. Cl.
*A61K 39/395* (2006.01)
*C07K 16/18* (2006.01)
*C07K 16/30* (2006.01)
*A61K 39/00* (2006.01)

(52) U.S. Cl.
CPC .............. *C07K 16/18* (2013.01); *C07K 16/30* (2013.01); *A61K 2039/505* (2013.01); *C07K 2317/55* (2013.01); *C07K 2317/92* (2013.01)

(58) Field of Classification Search
None
See application file for complete search history.

(56) References Cited

U.S. PATENT DOCUMENTS

| 4,485,045 A | 11/1984 | Regen |
| 4,544,545 A | 10/1985 | Ryan et al. |
| 5,013,556 A | 5/1991 | Woodle et al. |
| 5,595,760 A | 1/1997 | Cherif-Cheikh |
| 5,672,659 A | 9/1997 | Shalaby et al. |
| 2007/0117133 A1 | 5/2007 | Trieu et al. |
| 2009/0004192 A1 | 1/2009 | Pedersen et al. |
| 2009/0280128 A1 | 11/2009 | Kamogawa et al. |

FOREIGN PATENT DOCUMENTS

| EP | 1 813 943 A1 | 8/2007 |
| WO | WO 2011/153431 A2 | 12/2011 |

OTHER PUBLICATIONS

White et al. (2001, Ann. Rev. Med., 2001, 52:125-145).*
Meibohm (Pharmacokinetics and Pharmacodynamics of Biotech Drugs, Wiley-VHC, 2006, chapter 3, p. 45-91).*
Stancovski et al (PNAS, 1991, 88:8691-8695).*
Rempel et al (Clinical Cancer Research, 1999, 5:237-241).*
Bellahcéne et al., *Am. J. Path.*, 146, 95-100 (Jan. 1995).
Greenwald et al., *Adv. Drug. Del. Rev.*, 55, 217-250 (2003).
Kim et al., *J. Kor. Med. Sci.*, 13, 652-657 (1998).
Lane et al., *FASEB J.*, 8, 163-173 (1994).
Porter et al., *J. Histochem. and Cytochem.*, 43(8), 791-800 (1995).
*Remington's Pharmaceutical Sciences*, pp. 1438-1498 and 1553-1613, Easton, PA, Mack Publishing Co. (1980).
Rempel et al., *Clin. Cancer Res.*, 5, 237-241 (Feb. 1999).
Rezler et al., *J. Am. Chem. Soc.*, 129, 4961-4972 (2007).
Rudikoff et al., *Uniprot Direct Submission, Accession P01678* (Aug. 13, 1987).
Samad et al., *Curr. Drug Delivery*, 4, 297-305 (2007).
Schnitzer et al., *J. Biol. Chem.*, 269(8), 6072-6082 (Feb. 25, 1994).
Werle et al., *Int. J. Pharmaceutics*, 370, 26-32 (2009).
Yamanaka et al., *J. Urol.*, 166, 2495-2499 (Dec. 2001).
Maillard et al., *Bone*, 13, 257-264 (1992).
Sweetwyne et al., *J. Histochem. & Cytochem.*, 52, 723-733 (Jun. 2004).
European Patent Application No. 11775500.9 Search Report (Sep. 11, 2013).

* cited by examiner

*Primary Examiner* — Laura B Goddard
(74) *Attorney, Agent, or Firm* — Leydig, Voit & Mayer, Ltd.

(57) ABSTRACT

The invention provides SPARC binding antibodies that target disease sites, in particular, tumors and uses thereof to diagnose and treat diseases, in particular, cancerous tumors.

15 Claims, 21 Drawing Sheets

Figure 2

Fab 6 SEQ ID NO 15

(1) VH-
Protein sequence:
1 QVQLVQSGGG LVQPGGSLRL SCAASGFTVS SNYMSWVRQA PGKGLEWVSV
                                    H1
51 IYSGGSTYYA DSVKGRFTIS RDNSKNTLYL QMNSLRAEDT AVYYCARGIA
       H2
101 AAGLDYWGQG TLVTVSPAS
         H3

(2) VL-
Protein sequence:
1 EIVLTQSPSV SAAPGQRVTI SCSGSSSNIG NNYVSWYQQL PGTAPKLLIY
                                   L1
51 RNNQRPSGVP DRFSGSKSGT SASLAISGLR SEDEADYYCA AWDDSLSGWV
    L2                                                L3
101 FGGGKLTVL Fab 16 SEQ ID NO 16

(1) VH-
Protein sequence:
1 QVQLVQSGGG LVQPGGSLRL SCAASGFTVS SNYMSWVRQA PGKGLEWVSV
                                    H1
51 IYSGGSTYYA DSVKGRFTIS RDNSKNTLYL QMNSLRAEDT AVYYCARGIA
       H2
101 AAGLDYWGQG TLVTVSSAS
         H3

(2) VL-
Protein sequence:
1 EIVLTQPPSV SGTPGQRVTI SCSGSSSNIG SNYVYWYQQL PGTAPKLLIY
                                   L1
51 RNNQRPSGVP DRFSGSKSGT SASLAISGLR SEDEADYYCA AWDDSLSGWV
    L2                                                L3
101 FGGGKLTVL

Figure 4

Fab16 in pBAD  SEQ ID NO 17

VL-CL:
MKKTAIAIAVALAGFATVAQAAELVLTQPPSVSGTPGQRVTISCSGSSSNIGSNYVYWYQQLPGTAPKLLIYRN
NQRPSGVPDRFSGSKSGTSASLAISGLRSEDEADYCAAWDDSLSGWVFGGGTKLTVLGQPKAAPSVTLFPPSS
EELQANKATLVCLISDFYPGAVTVAWKADGSPVKAGVETTTPSKQSNNKYAASSYLSLTPEQWKSHRSYSCQVT
HEGSTVEKTVAPTECS

VH-CH1:
MKYLLPTAAAGLLLLAAQPAMAQVQLVQSGGGLIQPGGSLRLSCAASGFTVSSNYMSWVRQAPGKGLEWVSVIY
SGGSTYYADSVKGRFTISRDNSKNTLYLQMNSLRAEDTAVYYCARGIAAAGLDYWGQGTLVTVSSASTKGPSVF
PLAPSSKSTSGGTAALGCLVKDYFPEPVTVSWNSGALTSGVHTFPAVLQSSGLYSLSSVVTVPSSSLGTQTYIC
NVNHKPSNTKVDKKVEPKSCDKTSGQAGQHHHHHHGAYPDYDVPDYAS

Fab 16 = SEQ ID NO 20

Figure 15: Peptide Sequences from Phage Display Library against Imm-series Aligned against SPARC

| | mAb | pAb | Imm 1 | Imm 2 | Imm 3 | Imm 4 | Imm 7 |
|---|---|---|---|---|---|---|---|
| #1 | GLQSNSYRSLIM SEQ ID NO: 18 | NMNLTPFDHWND SEQ ID NO: 36 | HRTRSTVRSHTL SEQ ID NO: 55 | NFHYLSHAMTPN SEQ ID NO: 70 | KNHGATRTTRAS SEQ ID NO: 84 | DSNTWMYNFYSY SEQ ID NO: 85 | HPHKHKTHPPMV SEQ ID NO: 104 |
| | DRLQSLSYRTAL SEQ ID NO: 19 | YEDPSSLFTWND SEQ ID NO: 37 | IDRKRPYSRDNL SEQ ID NO: 56 | LPHVTHRHHHKF SEQ ID NO: 71 | DSNTWMYNFYSY SEQ ID NO: 85 | SEQ ID NO: 85 | SSIQWNPYFTPK SEQ ID NO: 105 |
| #2 | TNGPWPGAMTNP SEQ ID NO: 20 | ADTSHLSWRWND SEQ ID NO: 38 | ELSVIQKWRFFS SEQ ID NO: 57 | AYPTQTVARAMT SEQ ID NO: 72 | DSNTWMYNFYSY SEQ ID NO: 85 | HWGNHSKSHPQR SEQ ID NO: 77 | RIRQHKHNRQKG SEQ ID NO: 106 |
| #3 | GHYQSQSYRSPD SEQ ID NO: 21 | NDTPFKARNWED SEQ ID NO: 39 | ELSRIRSGVFCR SEQ ID NO: 58 | GHGWWAKHPRTL SEQ ID NO: 73 | HKTDSQKVFPVS SEQ ID NO: 86 | SYLQSKSYFLPP SEQ ID NO: 96 | WPHHFSLHWRNP SEQ ID NO: 107 |
| #4 | GPTAYSYRFAQP SEQ ID NO: 22 | YSSYNSSHLWTD SEQ ID NO: 40 | AETVESCLAKSH SEQ ID NO: 59 | WHKHPSFSGRHN SEQ ID NO: 74 | GLHKHHLMHKWR SEQ ID NO: 87 | DSNTWMYNFYSY SEQ ID NO: 85 | SVHRRLRWRALK SEQ ID NO: 108 |
| #5 | TNGPWPGAMTNP SEQ ID NO: 20 | ASQLNDYFSWND SEQ ID NO: 41 | DLPTLNARPPIF SEQ ID NO: 60 | APHHLSWRHHHS SEQ ID NO: 75 | DSNTWMYNFYSY SEQ ID NO: 85 | THVSPRLTAPMV SEQ ID NO: 97 | VSRHQSWHPHDL SEQ ID NO: 109 |
| #6 | DLVSSSYRGSII SEQ ID NO: 23 | TPIYLPNSMWDD SEQ ID NO: 42 | ELSVIQKWRFFS SEQ ID NO: 57 | AYPTQTVARAMT SEQ ID NO: 72 | FHKPSWHAWSGR SEQ ID NO: 88 | HFRHMHQVVGGP SEQ ID NO: 98 | WPGFFHSHRTGP SEQ ID NO: 110 |
| #7 | GLQSNSYRSLIM SEQ ID NO: 18 | SHETSITVLSQV SEQ ID NO: 43 | HTSWRHHPTLPS SEQ ID NO: 61 | HWGNHSKSHPQR SEQ ID NO: 77 | DSNTWMYNFYSY SEQ ID NO: 85 | GHWSSWHHQKRP SEQ ID NO: 64 | WHTNHKQHWRHT SEQ ID NO: 111 |
| #8 | NTAYQSYSYRAI SEQ ID NO: 24 | TPFSNHTFGDGF SEQ ID NO: 44 | WHKPHARPALDL SEQ ID NO: 62 | LHRHPHPHTIPP SEQ ID NO: 78 | KLWHHHPSRYI SEQ ID NO: 89 | DSNTWMYNFYSY SEQ ID NO: 85 | |
| #9 | WTSYSYRVGTLA SEQ ID NO: 25 | TPWNNSEQRWHD SEQ ID NO: 45 | GHGYWASKFWQK SEQ ID NO: 63 | HWGNHSKSHPQR SEQ ID NO: 77 | HHKSWITKGMPP SEQ ID NO: 90 | SPLTVPYERKLL SEQ ID NO: 99 | WPHHHHTRLSTV SEQ ID NO: 112 |
| #10 | NPLVSHSYRPDW SEQ ID NO: 26 | GTPAMLKMKWDD SEQ ID NO: 46 | GHWSSWHHQKRP SEQ ID NO: 64 | AYPTQTVARAMT SEQ ID NO: 72 | FHKPHMPFQSNR SEQ ID NO: 91 | DSNTWMYNFYSY SEQ ID NO: 85 | FPTWKPWHRTHL SEQ ID NO: 113 |
| #11 | VPWGLSYRPVGA SEQ ID NO: 27 | NPEHLWHTRWGD SEQ ID NO: 47 | HVLHKHGHLQKN SEQ ID NO: 65 | AYPTQTVARAMT SEQ ID NO: 72 | DSNTWMYNFYSY SEQ ID NO: 85 | FPKWYHGHVNRS SEQ ID NO: 100 | FHRHHSPPPSII SEQ ID NO: 114 |
| #12 | LQSTSYRLTNSH SEQ ID NO: 28 | DQQLIHSAGWSD SEQ ID NO: 48 | AETVESCLAKSH SEQ ID NO: 59 | GHGYWASKFWQK SEQ ID NO: 63 | AHPHFKHTHHRP SEQ ID NO: 92 | DSNTWMYNFYSY SEQ ID NO: 85 | WPHHHHTRLSTV SEQ ID NO: 112 |
| #13 | ATAPTSHSYRSI SEQ ID NO: 29 | ITTKAYNIKWSD SEQ ID NO: 49 | NQGPHLSIPSTS SEQ ID NO: 66 | HWKPWPTARFQT SEQ ID NO: 79 | LPFHNHKYWNRL SEQ ID NO: 93 | DSNTWMYNFYSY SEQ ID NO: 85 | HHWKFFSHPGA SEQ ID NO: 115 |
| #14 | ELASHAYRTHAS SEQ ID NO: 30 | NMNLTPFDHWND SEQ ID NO: 36 | APIWHKHRPHHQ SEQ ID NO: 67 | HGMKHWSWKSN SEQ ID NO: 80 | GLHKHHLMHKWR SEQ ID NO: 87 | VEAHKRPWNFFR SEQ ID NO: 101 | FHRHPHPHNLIR SEQ ID NO: 116 |
| #15 | THNLKWPEEYYR SEQ ID NO: 31 | TTNNMNITSWED SEQ ID NO: 50 | FHKHPSHMWRLS SEQ ID NO: 68 | HWGNHSKSHPQR SEQ ID NO: 77 | QNLMDQMPPPVH SEQ ID NO: 94 | DSNTWMYNFYSY SEQ ID NO: 85 | HISHKNLHRWIK SEQ ID NO: 117 |
| #16 | THYNSLASVSYR SEQ ID NO: 32 | LGMGTPIHEWND SEQ ID NO: 51 | SWWHKTSPHHHR SEQ ID NO: 69 | WPSHRHIHPAPV SEQ ID NO: 81 | HWDYVRQLSLVQ SEQ ID NO: 95 | DSNTWMYNFYSY SEQ ID NO: 85 | WPHHFSLHWRNP SEQ ID NO: 107 |
| #17 | VLTSASYRFMAP SEQ ID NO: 33 | WPASLYAAEWED SEQ ID NO: 52 | ELSVIQKWRFFS SEQ ID NO: 57 | FGPSTYPWTLYA SEQ ID NO: 82 | WHKHPSFSGRHN SEQ ID NO: 74 | DSNTWMYNFYSY SEQ ID NO: 85 | WHKHIPSIRFPS SEQ ID NO: 118 |
| #18 | YPMISSSYRMTT SEQ ID NO: 34 | NMNLTPYDHWND SEQ ID NO: 53 | NHFSWSTPPSAE SEQ ID NO: 57 | AYPTQTVARAMT SEQ ID NO: 72 | AETVESCLAKSH SEQ ID NO: 59 | YMPANQSALPHR SEQ ID NO: 102 | TKRFKWRPWRGV SEQ ID NO: 119 |
| #19 | QHHFISSSYRPS SEQ ID NO: 35 | SNMIYFWREIPE SEQ ID NO: 54 | WHKHPSFSGRHN SEQ ID NO: 75 | WVPHHHHRATKT SEQ ID NO: 83 | GLHKHHLMHKWR SEQ ID NO: 87 | KPYPYPAARILP SEQ ID NO: 103 | HISHKNLHRWIK SEQ ID NO: 117 |

Figure 16 - Peptide Sequences from Phage Display Library against Imm-series Aligned against SPARC

|  | Imm 9 | Imm 10 | Imm 11 | Imm 12 | Imm 13 | Imm 14 |
|---|---|---|---|---|---|---|
| #1 | HWGNHSKSHPQR SEQ ID NO: 77 | DHVRETNDRTTS SEQ ID NO: 133 | HMPLIRQPYWND SEQ ID NO: 153 | MVHQRHHYLLSQ SEQ ID NO: 166 | LPQRLGVGEKDY SEQ ID NO: 179 | FPPSWLAASNRP SEQ ID NO: 188 |
| #2 | HWGNHSKSHPQR SEQ ID NO: 77 | STSSISHGSNGR SEQ ID NO: 134 | GTSTFNSVPVRD SEQ ID NO: 154 | WIPPQWSRLIEP SEQ ID NO: 167 | AFDLHMLLERDR SEQ ID NO: 180 | SFMMQTEPLARH SEQ ID NO: 189 |
| #3 | KHLHAPGWYTRM SEQ ID NO: 120 | EDVLRWHPEWPG SEQ ID NO: 135 | MPKPMISDHLRY SEQ ID NO: 155 | VLELGVPPPSRA SEQ ID NO: 168 | AFDLHMLLERDR SEQ ID NO: 180 | MQDPQVQRRILH SEQ ID NO: 190 |
| #4 | HWWKHPTRYSLG SEQ ID NO: 121 | TPPWAHSRQNMY SEQ ID NO: 136 | SSYDWKAQPRAS SEQ ID NO: 156 | QPRPSIISHYWT SEQ ID NO: 169 | AFDLHMLLERDR SEQ ID NO: 180 | AVSPFLAPVDLP SEQ ID NO: 191 |
| #5 | WVPHHHHRATKT SEQ ID NO: 83 | IQKEFLHKPHSL SEQ ID NO: 137 | LPHPLSSIEWHD SEQ ID NO: 157 | QFNTRDGIYSTH SEQ ID NO: 170 | AFDLHMLLERDR SEQ ID NO: 180 | EHSTYKGSPLYP SEQ ID NO: 192 |
| #6 | SIVPTNFFYPPV SEQ ID NO: 122 | HETHALSLENRR SEQ ID NO: 138 | AIAHTSYAITTP SEQ ID NO: 158 |  | AETVESCLAKSH SEQ ID NO: 59 | LLADTTHHRPWT SEQ ID NO: 193 |
| #7 | GHYPWWKNHMRS SEQ ID NO: 123 | GAADLANTTLRR SEQ ID NO: 139 | TTVSFSLARDHL SEQ ID NO: 159 | MPMGFKPVKFRA SEQ ID NO: 171 | VWLPEEKDRTTD SEQ ID NO: 181 | TYHESQTSFTNT SEQ ID NO: 194 |
| #8 | WPQTATRTSLLS SEQ ID NO: 124 | DTPNSFISWHAP SEQ ID NO: 140 | SITITVSHPPAP SEQ ID NO: 160 | SYTTHPELNANM SEQ ID NO: 172 | AFDLHMLLERDR SEQ ID NO: 180 | NTHDARNPLDYN SEQ ID NO: 195 |
| #9 | VPNKLSSSYWHQ SEQ ID NO: 125 | HQVHMPTIAVFS SEQ ID NO: 141 | EWTRVYAPFNGY SEQ ID NO: 161 | VYADVLTYGSSF SEQ ID NO: 164 | AFDLHMLLERDR SEQ ID NO: 180 | DKSVSPLLVGRA SEQ ID NO: 196 |
| #10 | FHKHPHSGRWYP SEQ ID NO: 126 | AHTTNMLLLRTT SEQ ID NO: 142 | AAWNDRLIATVE SEQ ID NO: 162 | SAHGTSTGVPWP SEQ ID NO: 173 | YPSAPPQWLTNT SEQ ID NO: 182 | LGFDPTSTRFYT SEQ ID NO: 197 |
| #11 | GYFPHWHKRTPG SEQ ID NO: 127 | HTSYFQYYAETP SEQ ID NO: 143 | SGHQLLLNKMPN SEQ ID NO: 163 | VYADVLTYGSSF SEQ ID NO: 164 | QSYHDNTGERDP SEQ ID NO: 183 | IARAHPPLGLNS SEQ ID NO: 198 |
| #12 | YNSTIRIVSTEI SEQ ID NO: 128 | SIPKHWSATDES SEQ ID NO: 144 | VYADVLTYGSSF SEQ ID NO: 164 | ASSMHHNYSVNL SEQ ID NO: 174 | FDDNQPRQFKIP SEQ ID NO: 184 | AETVESCLAKSH SEQ ID NO: 59 |
| #13 | SIVPTNFFYPPV SEQ ID NO: 122 | KHHHYFHHAGLR SEQ ID NO: 145 | SGHQLLLNKMPN SEQ ID NO: 163 | QDRLPNRWHTYI SEQ ID NO: 175 | NHGERDRSFFLQ SEQ ID NO: 185 | VTQPNERDYHRS SEQ ID NO: 199 |
| #14 | SPKQPLTGPLVF SEQ ID NO: 129 | IPMKPDDKSLAQ SEQ ID NO: 146 | SGHQLLLNKMPN SEQ ID NO: 163 | HPSQSPSTRDPW SEQ ID NO: 176 | AFDLHMLLERDR SEQ ID NO: 180 | LLADTTHHRPWT SEQ ID NO: 193 |
| #15 | AKLPWHHHHGRP SEQ ID NO: 130 | HQMPSPLPERQL SEQ ID NO: 147 |  | AAWNDRLIATVE SEQ ID NO: 162 | NTRLTTITHPTP SEQ ID NO: 186 | FVSVGMKPSPRP SEQ ID NO: 200 |
| #16 | KPPQNTSAPYLP SEQ ID NO: 131 | TVANTLMTPPLP SEQ ID NO: 148 | SGHQLLLNKMPN SEQ ID NO: 163 | VYADVLTYGSSF SEQ ID NO: 164 | AFDLHMLLERDR SEQ ID NO: 180 | HVIVGMKYEFLG SEQ ID NO: 201 |
| #17 | GHWSSWHHQKRP SEQ ID NO: 64 | YPLHSQGSKEGQ SEQ ID NO: 149 | SGHQLLLNKMPN SEQ ID NO: 163 | SAQFSLLKFPVF SEQ ID NO: 177 | AETVESCLAKSH SEQ ID NO: 59 | ASNFRMPELQSA SEQ ID NO: 202 |
| #18 | WVPHHHHRATKT SEQ ID NO: 83 | GLYHEQVSKPNT SEQ ID NO: 150 | GTSTFNSVPVRD SEQ ID NO: 154 | IVQPSMRAWNYV SEQ ID NO: 178 | NHGERDRSFFLQ SEQ ID NO: 185 | SILSTMSPHGAT SEQ ID NO: 203 |
| #19 | AETVESCLAKSH SEQ ID NO: 59 | NTDNRPDVPGNF SEQ ID NO: 151 | QRPADMGTGALK SEQ ID NO: 165 |  | AFDLHMLLERDR SEQ ID NO: 180 | HSIKHTNAFQAP SEQ ID NO: 204 |
| #20 | HPRAAPLAYRSA SEQ ID NO: 132 | GDRWERVSVTKL SEQ ID NO: 152 | SGHQLLLNKMPN SEQ ID NO: 163 | SAHGTSTGVPWP SEQ ID NO: 173 | LPSPSPPRILQP SEQ ID NO: 187 | IVVPYHQDSMKP SEQ ID NO: 205 |

Fab 6 (SEQ ID NO 15)    Imm-13

Fab 16 (SEQ ID NO 16) → Imm-14

SEQUENCE LISTING

```
<160> NUMBER OF SEQ ID NOS: 205

<210> SEQ ID NO 1
<211> LENGTH: 92
<212> TYPE: PRT
<213> ORGANISM: Artificial Sequence
<220> FEATURE:
<223> OTHER INFORMATION: Synthetic

<400> SEQUENCE: 1
```

-continued

```
Lys Ala Thr Gly Tyr Thr Phe Ser Asn Tyr Trp Val Glu Trp Val Lys
1               5                   10                  15

Gln Arg Pro Gly His Gly Leu Glu Trp Ile Gly Glu Ile Leu Pro Gly
            20                  25                  30

Ile Ser Ser Thr Asn Tyr Asp Glu Lys Phe Lys Asp Lys Ala Thr Phe
        35                  40                  45

Thr Ala Asp Thr Ser Ser Asn Thr Ala Tyr Met Gln Leu Ser Ser Leu
50                  55                  60

Thr Ser Glu Asp Ser Ala Val Tyr Tyr Cys Ser Arg Gly Arg Pro Ala
65                  70                  75                  80

Trp Ser Ala Phe Trp Gly Gln Gly Thr Thr Val Thr
                85                  90
```

<210> SEQ ID NO 2
<211> LENGTH: 92
<212> TYPE: PRT
<213> ORGANISM: Artificial Sequence
<220> FEATURE:
<223> OTHER INFORMATION: Synthetic

<400> SEQUENCE: 2

```
Thr Val Thr Gly Tyr Ser Ile Thr Ser Asp His Ala Trp Ser Trp Ile
1               5                   10                  15

Arg Gln Phe Pro Gly Asn Lys Leu Glu Trp Met Gly Tyr Ile Ser Tyr
            20                  25                  30

Ser Gly Ser Thr Ser Tyr Asn Pro Ser Leu Lys Ser Arg Val Ser Val
        35                  40                  45

Thr Arg Asp Thr Ser Lys Asn His Phe Phe Leu Gln Leu Asn Ser Val
50                  55                  60

Thr Thr Glu Asp Thr Ala Thr Tyr Tyr Cys Ala Arg Ala Ala Phe Ile
65                  70                  75                  80

Gly Gly Trp Phe Ala Tyr Trp Gly Gln Gly Thr Thr
                85                  90
```

<210> SEQ ID NO 3
<211> LENGTH: 92
<212> TYPE: PRT
<213> ORGANISM: Artificial Sequence
<220> FEATURE:
<223> OTHER INFORMATION: Synthetic

<400> SEQUENCE: 3

```
Thr Val Thr Gly Tyr Ser Ile Thr Ser Asp His Ala Trp Ser Trp Ile
1               5                   10                  15

Arg Gln Phe Pro Gly Asn Lys Leu Glu Trp Met Gly Tyr Ile Ser Tyr
            20                  25                  30

Ser Gly Ser Thr Ser Tyr Asn Pro Ser Leu Lys Ser Arg Val Ser Val
        35                  40                  45

Thr Arg Asp Thr Ser Lys Asn His Phe Phe Leu Gln Leu Asn Ser Val
50                  55                  60

Thr Thr Glu Asp Thr Ala Thr Tyr Tyr Cys Ala Arg Ala Ala Phe Ile
65                  70                  75                  80

Gly Gly Trp Phe Ala Tyr Trp Gly Gln Gly Thr Thr
                85                  90
```

<210> SEQ ID NO 4
<211> LENGTH: 92
<212> TYPE: PRT

<213> ORGANISM: Artificial Sequence
<220> FEATURE:
<223> OTHER INFORMATION: Synthetic

<400> SEQUENCE: 4

```
Ala Ala Ser Gly Phe Ala Phe Ser Ser Tyr Asp Met Ser Trp Val Arg
1               5                   10                  15

Gln Thr Pro Glu Lys Arg Leu Glu Trp Val Ala Tyr Ile Thr Ser Gly
            20                  25                  30

Gly Gly Ser Thr Tyr Tyr Pro Asp Thr Val Lys Gly Arg Phe Thr Ile
        35                  40                  45

Ser Arg Asp Asn Ala Lys Asn Thr Leu Tyr Leu Gln Met Ser Ser Leu
50                  55                  60

Lys Ser Glu Asp Thr Ala Met Tyr Tyr Cys Ala Gly Ser Arg Ser Trp
65                  70                  75                  80

Phe Ala Tyr Trp Gly Gln Gly Thr Thr Val Thr Val
                85                  90
```

<210> SEQ ID NO 5
<211> LENGTH: 92
<212> TYPE: PRT
<213> ORGANISM: Artificial Sequence
<220> FEATURE:
<223> OTHER INFORMATION: Synthetic

<400> SEQUENCE: 5

```
Thr Val Thr Gly Tyr Ser Ile Thr Ser Asp Ser Ala Trp Asn Trp Ile
1               5                   10                  15

Arg Gln Phe Pro Gly Asn Lys Leu Glu Trp Met Gly His Ile Ser Tyr
            20                  25                  30

Ser Gly Ser Thr Ser Tyr Asn Pro Ser Leu Lys Ser Arg Ile Ser Ile
        35                  40                  45

Thr Arg Asp Thr Ser Lys Asp Gln Phe Phe Leu Gln Leu Asn Ser Val
50                  55                  60

Thr Thr Glu Asp Thr Ala Thr Tyr Tyr Cys Ala Arg Gly Ser Tyr Tyr
65                  70                  75                  80

Gly Asn Phe Gly Phe Thr Tyr Trp Gly Gln Gly Thr
                85                  90
```

<210> SEQ ID NO 6
<211> LENGTH: 92
<212> TYPE: PRT
<213> ORGANISM: Artificial Sequence
<220> FEATURE:
<223> OTHER INFORMATION: Synthetic

<400> SEQUENCE: 6

```
Ala Ala Ser Gly Phe Thr Phe Ser Tyr Tyr Gly Met Ser Trp Val Arg
1               5                   10                  15

Gln Thr Pro Asp Lys Arg Leu Glu Trp Val Ala Thr Ile Ser Ser Gly
            20                  25                  30

Gly Ser Tyr Thr Tyr Tyr Pro Asp Ser Val Lys Gly Arg Phe Thr Ile
        35                  40                  45

Ser Arg Asp Asn Ser Glu Asn Thr Leu Tyr Leu Gln Met Asn Ser Leu
50                  55                  60

Lys Ser Glu Asp Thr Ala Met Tyr Phe Cys Ala Arg Arg Gly Ser Ser
65                  70                  75                  80

Gly Asp Tyr Tyr Gly Met Asp Tyr Trp Gly Gln Gly
                85                  90
```

```
<210> SEQ ID NO 7
<211> LENGTH: 92
<212> TYPE: PRT
<213> ORGANISM: Artificial Sequence
<220> FEATURE:
<223> OTHER INFORMATION: Synthetic

<400> SEQUENCE: 7

Lys Ala Ser Gly Tyr Thr Phe Thr Lys Tyr Gly Met Asn Trp Val Lys
1               5                   10                  15

Gln Ala Pro Gly Lys Gly Leu Gln Trp Met Gly Trp Ile Asn Thr Asn
            20                  25                  30

Thr Gly Glu Pro Thr Tyr Ala Glu Glu Phe Lys Gly Arg Phe Ala Phe
        35                  40                  45

Ser Leu Glu Thr Ser Ala Ser Thr Ala Tyr Leu Gln Ile Asn Asn Leu
    50                  55                  60

Glu Asn Ala Asp Ser Ala Thr Tyr Phe Cys Thr Arg Gly Ser Ser Tyr
65                  70                  75                  80

Phe Asp Tyr Trp Gly Gln Gly Thr Thr Val Thr Val
                85                  90

<210> SEQ ID NO 8
<211> LENGTH: 92
<212> TYPE: PRT
<213> ORGANISM: Artificial Sequence
<220> FEATURE:
<223> OTHER INFORMATION: Synthetic

<400> SEQUENCE: 8

Gly Asp Ser Val Ser Leu Ser Cys Arg Ala Ser Gln Ser Ile Ser Asn
1               5                   10                  15

Asn Leu His Trp Tyr Gln Gln Lys Ser His Glu Ser Pro Arg Leu Leu
            20                  25                  30

Ile Lys Tyr Ala Ser Gln Ser Ile Ser Gly Ile Pro Ser Arg Phe Ser
        35                  40                  45

Gly Ser Gly Ser Gly Thr Asp Phe Thr Leu Ser Ile Asn Ser Val Glu
    50                  55                  60

Thr Glu Asp Phe Gly Met Tyr Phe Cys Gln Gln Ser Asn Ser Trp Pro
65                  70                  75                  80

Leu Thr Phe Gly Gly Gly Thr Lys Leu Glu Leu Lys
                85                  90

<210> SEQ ID NO 9
<211> LENGTH: 92
<212> TYPE: PRT
<213> ORGANISM: Artificial Sequence
<220> FEATURE:
<223> OTHER INFORMATION: Synthetic

<400> SEQUENCE: 9

Gly Glu Lys Val Thr Ile Thr Cys Ser Ala Ser Ser Ser Val Ser Tyr
1               5                   10                  15

Met His Trp Phe Gln Gln Lys Pro Gly Thr Ser Pro Lys Leu Trp Ile
            20                  25                  30

Tyr Ser Thr Pro Asn Leu Ala Ser Gly Val Pro Ala Arg Phe Ser Gly
        35                  40                  45

Ser Gly Ser Gly Thr Ser Tyr Ser Leu Thr Ile Ser Arg Met Glu Ala
    50                  55                  60
```

Glu Asp Ala Ala Thr Tyr Tyr Cys Gln Gln Arg Ser Ser Tyr Pro Leu
65                  70                  75                  80

Thr Phe Gly Gly Gly Thr Lys Leu Glu Leu Lys Gln
                85                  90

<210> SEQ ID NO 10
<211> LENGTH: 92
<212> TYPE: PRT
<213> ORGANISM: Artificial Sequence
<220> FEATURE:
<223> OTHER INFORMATION: Synthetic

<400> SEQUENCE: 10

Gly Gln Lys Val Thr Ile Thr Cys Ser Ala Ser Ser Val Ser Tyr
1               5                   10                  15

Met His Trp Tyr Gln Gln Lys Ser Gly Thr Ser Pro Lys Pro Trp Ile
                20                  25                  30

Tyr Glu Ile Ser Lys Leu Ala Ser Gly Val Pro Ala Arg Phe Ser Gly
            35                  40                  45

Ser Gly Ser Gly Thr Ser Tyr Ser Leu Thr Ile Ser Ser Met Glu Ala
        50                  55                  60

Glu Asp Ala Ala Ile Tyr Tyr Cys Gln Gln Trp Asn Tyr Pro Leu Ile
65                  70                  75                  80

Thr Phe Gly Gly Gly Thr Lys Leu Glu Leu Lys Arg
                85                  90

<210> SEQ ID NO 11
<211> LENGTH: 92
<212> TYPE: PRT
<213> ORGANISM: Artificial Sequence
<220> FEATURE:
<223> OTHER INFORMATION: Synthetic

<400> SEQUENCE: 11

Gly Glu Gly Val Ser Phe Ser Cys Arg Ala Ser Gln Ser Ile Gly Thr
1               5                   10                  15

Gly Ile His Trp Tyr Gln Arg Arg Thr Asn Gly Ser Pro Arg Leu Leu
                20                  25                  30

Ile Lys Tyr Ala Ser Glu Ser Ile Ser Gly Ile Pro Ser Arg Phe Ser
            35                  40                  45

Gly Ser Gly Ser Gly Thr Asp Phe Thr Leu Thr Ile Asn Ser Val Glu
        50                  55                  60

Ser Glu Asp Ile Ala Asp Tyr Tyr Cys Gln Gln Ser Tyr Ser Trp Pro
65                  70                  75                  80

Leu Thr Phe Gly Ala Gly Thr Lys Leu Glu Leu Lys
                85                  90

<210> SEQ ID NO 12
<211> LENGTH: 91
<212> TYPE: PRT
<213> ORGANISM: Artificial Sequence
<220> FEATURE:
<223> OTHER INFORMATION: Synthetic

<400> SEQUENCE: 12

Gly Glu Thr Val Thr Ile Thr Cys Gln Ala Ser Glu Asn Ile Ala Ser
1               5                   10                  15

Asp Leu Ala Trp Tyr Gln Lys Glu Gly Arg Ser Pro Gln Leu Leu Val
                20                  25                  30

Tyr Glu Ala Arg Asn Leu Ala Asp Gly Val Pro Ser Arg Phe Ser Gly

```
                35                  40                  45
Ser Gly Ser Asp Thr Leu Tyr Ser Leu Asn Ile His Ser Leu Gln Ser
         50                  55                  60

Glu Asp Val Ala Arg Tyr Tyr Cys Gln His Tyr Tyr Gly Thr Pro Trp
 65                  70                  75                  80

Thr Phe Gly Gly Gly Thr Lys Pro Arg Ala Asn
                 85                  90

<210> SEQ ID NO 13
<211> LENGTH: 92
<212> TYPE: PRT
<213> ORGANISM: Artificial Sequence
<220> FEATURE:
<223> OTHER INFORMATION: Synthetic

<400> SEQUENCE: 13

Gly Glu Lys Val Thr Met Ser Cys Lys Ser Gln Ser Leu Leu Tyr
 1               5                  10                  15

Ser Asn Ser Gln Lys Asn Tyr Leu Ala Trp Tyr Gln Gln Lys Pro Gly
                 20                  25                  30

Gln Ser Pro Lys Leu Leu Ile Tyr Trp Ala Ser Thr Arg Glu Ser Gly
             35                  40                  45

Val Pro Pro Arg Phe Thr Gly Ser Gly Ser Gly Thr Asp Phe Ser Leu
         50                  55                  60

Thr Ile Ser Ser Val Lys Ala Glu Asp Leu Ala Val Tyr Tyr Cys Gln
 65                  70                  75                  80

Gln Tyr Tyr Ser Phe Pro Arg Thr Phe Gly Gly Gly
                 85                  90

<210> SEQ ID NO 14
<211> LENGTH: 92
<212> TYPE: PRT
<213> ORGANISM: Artificial Sequence
<220> FEATURE:
<223> OTHER INFORMATION: Synthetic

<400> SEQUENCE: 14

Gly Gln Arg Ala Thr Ile Ser Tyr Arg Ala Ser Lys Ser Val Ser Thr
 1               5                  10                  15

Ser Gly Tyr Ser Tyr Met His Trp Asn Gln Gln Lys Pro Gly Gln Pro
                 20                  25                  30

Pro Arg Leu Leu Ile Tyr Leu Val Ser Asn Leu Glu Ser Gly Val Pro
             35                  40                  45

Ala Arg Phe Ser Gly Ser Gly Ser Gly Thr Asp Phe Thr Leu Asn Ile
         50                  55                  60

His Pro Val Glu Glu Asp Ala Ala Thr Tyr Tyr Cys Gln His Ile
 65                  70                  75                  80

Arg Glu Leu Thr Arg Ser Val Glu Ala Pro Ser Ser
                 85                  90

<210> SEQ ID NO 15
<211> LENGTH: 440
<212> TYPE: PRT
<213> ORGANISM: Artificial Sequence
<220> FEATURE:
<223> OTHER INFORMATION: Synthetic

<400> SEQUENCE: 15

Gln Val Gln Leu Val Gln Ser Gly Gly Gly Leu Val Gln Pro Gly Gly
 1               5                  10                  15
```

```
Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gly Ile Ala Ala Ala Gly Leu Asp Tyr Trp Gly Gln Gly Thr Leu
            100                 105                 110

Val Thr Val Ser Pro Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Val Cys Asn Val Asn His Lys Pro Ser Asn
        195                 200                 205

Thr Lys Val Asp Lys Lys Val Glu Pro Lys Ser Cys Asp Lys Thr Ser
210                 215                 220

Glu Leu Val Leu Thr Gln Pro Pro Ser Val Ser Ala Ala Pro Gly Gln
225                 230                 235                 240

Lys Val Thr Ile Ser Cys Ser Gly Ser Ser Ser Asn Ile Gly Asn Asn
                245                 250                 255

Tyr Val Tyr Trp Tyr Gln Gln Leu Pro Gly Thr Ala Pro Lys Leu Leu
            260                 265                 270

Ile Tyr Arg Asn Asn Gln Arg Pro Ser Gly Val Pro Asp Arg Phe Ser
        275                 280                 285

Gly Ser Lys Ser Gly Thr Ser Ala Ser Leu Ala Ile Ser Gly Leu Arg
290                 295                 300

Ser Glu Asp Glu Ala Asp Tyr Tyr Cys Ala Ala Trp Asp Asp Ser Leu
305                 310                 315                 320

Ser Gly Trp Val Phe Gly Gly Gly Thr Lys Leu Thr Val Leu Gly Gln
                325                 330                 335

Pro Lys Ala Ala Pro Ser Val Thr Leu Phe Pro Pro Ser Ser Glu Glu
            340                 345                 350

Leu Gln Ala Asn Lys Ala Thr Leu Val Cys Leu Ile Ser Asp Phe Tyr
        355                 360                 365

Pro Gly Ala Val Thr Val Ala Trp Lys Ala Asp Gly Ser Pro Val Lys
370                 375                 380

Ala Gly Val Glu Thr Thr Thr Pro Ser Lys Gln Ser Asn Asn Lys Tyr
385                 390                 395                 400

Ala Ala Ser Ser Tyr Leu Ser Leu Thr Pro Glu Gln Trp Lys Ser His
                405                 410                 415

Arg Ser Tyr Ser Cys Gln Val Thr His Glu Gly Ser Thr Val Glu Lys
            420                 425                 430
```

Thr Val Ala Pro Thr Glu Cys Ser
            435                 440

<210> SEQ ID NO 16
<211> LENGTH: 440
<212> TYPE: PRT
<213> ORGANISM: Artificial Sequence
<220> FEATURE:
<223> OTHER INFORMATION: Synthetic

<400> SEQUENCE: 16

Gln Val Gln Leu Val Gln Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Gly Ile Ala Ala Ala Gly Leu Asp Tyr Trp Gly Gln Gly Thr Leu
        100                 105                 110

Val Thr Val Ser Ser Ala Ser Thr Lys Gly Pro Ser Val Phe Pro Leu
    115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
        180                 185                 190

Leu Gly Thr Gln Thr Tyr Ile Cys Asn Val Asn His Lys Pro Ser Asn
    195                 200                 205

Thr Lys Val Asp Lys Lys Val Glu Pro Lys Ser Cys Asp Lys Thr Ser
210                 215                 220

Glu Leu Val Leu Thr Gln Pro Pro Ser Val Ser Gly Thr Pro Gly Gln
225                 230                 235                 240

Arg Val Thr Ile Ser Cys Ser Gly Ser Ser Ser Asn Ile Gly Ser Asn
            245                 250                 255

Tyr Val Tyr Trp Tyr Gln Gln Leu Pro Gly Thr Ala Pro Lys Leu Leu
        260                 265                 270

Ile Tyr Arg Asn Asn Gln Arg Pro Ser Gly Val Pro Asp Arg Phe Ser
    275                 280                 285

Gly Ser Lys Ser Gly Thr Ser Ala Ser Leu Ala Ile Ser Gly Leu Arg
290                 295                 300

Ser Glu Asp Glu Ala Asp Tyr Tyr Cys Ala Ala Trp Asp Asp Ser Leu
305                 310                 315                 320

Ser Gly Trp Val Phe Gly Gly Thr Lys Leu Thr Val Leu Gly Gln
            325                 330                 335

Pro Lys Ala Ala Pro Ser Val Thr Leu Phe Pro Pro Ser Ser Glu Glu
        340                 345                 350

```
Leu Gln Ala Asn Lys Ala Thr Leu Val Cys Leu Ile Ser Asp Phe Tyr
            355                 360                 365
Pro Gly Ala Val Thr Val Ala Trp Lys Ala Asp Gly Ser Pro Val Lys
        370                 375                 380
Ala Gly Val Glu Thr Thr Thr Pro Ser Lys Gln Ser Asn Asn Lys Tyr
385                 390                 395                 400
Ala Ala Ser Ser Tyr Leu Ser Leu Thr Pro Glu Gln Trp Lys Ser His
                405                 410                 415
Arg Ser Tyr Ser Cys Gln Val Thr His Glu Gly Ser Thr Val Glu Lys
            420                 425                 430
Thr Val Ala Pro Thr Glu Cys Ser
            435                 440

<210> SEQ ID NO 17
<211> LENGTH: 507
<212> TYPE: PRT
<213> ORGANISM: Artificial Sequence
<220> FEATURE:
<223> OTHER INFORMATION: Synthetic

<400> SEQUENCE: 17

Met Lys Lys Thr Ala Ile Ala Ile Ala Val Ala Leu Ala Gly Phe Ala
1               5                   10                  15
Thr Val Ala Gln Ala Ala Glu Leu Val Leu Thr Gln Pro Pro Ser Val
            20                  25                  30
Ser Gly Thr Pro Gly Gln Arg Val Thr Ile Ser Cys Ser Gly Ser Ser
        35                  40                  45
Ser Asn Ile Gly Ser Asn Tyr Val Tyr Trp Tyr Gln Gln Leu Pro Gly
    50                  55                  60
Thr Ala Pro Lys Leu Leu Ile Tyr Arg Asn Asn Gln Arg Pro Ser Gly
65                  70                  75                  80
Val Pro Asp Arg Phe Ser Gly Ser Lys Ser Gly Thr Ser Ala Ser Leu
                85                  90                  95
Ala Ile Ser Gly Leu Arg Ser Glu Asp Glu Ala Asp Tyr Tyr Cys Ala
            100                 105                 110
Ala Trp Asp Asp Ser Leu Ser Gly Trp Val Phe Gly Gly Gly Thr Lys
        115                 120                 125
Leu Thr Val Leu Gly Gln Pro Lys Ala Ala Pro Ser Val Thr Leu Phe
130                 135                 140
Pro Pro Ser Ser Glu Glu Leu Gln Ala Asn Lys Ala Thr Leu Val Cys
145                 150                 155                 160
Leu Ile Ser Asp Phe Tyr Pro Gly Ala Val Thr Val Ala Trp Lys Ala
                165                 170                 175
Asp Gly Ser Pro Val Lys Ala Gly Val Glu Thr Thr Thr Pro Ser Lys
            180                 185                 190
Gln Ser Asn Asn Lys Tyr Ala Ala Ser Ser Tyr Leu Ser Leu Thr Pro
        195                 200                 205
Glu Gln Trp Lys Ser His Arg Ser Tyr Ser Cys Gln Val Thr His Glu
    210                 215                 220
Gly Ser Thr Val Glu Lys Thr Val Ala Pro Thr Glu Cys Ser Met Lys
225                 230                 235                 240
Tyr Leu Leu Pro Thr Ala Ala Ala Gly Leu Leu Leu Leu Ala Ala Gln
                245                 250                 255
Pro Ala Met Ala Gln Val Gln Leu Val Gln Ser Gly Gly Gly Leu Ile
            260                 265                 270
```

```
Gln Pro Gly Gly Ser Leu Arg Leu Ser Cys Ala Ala Ser Gly Phe Thr
            275                 280                 285

Val Ser Ser Asn Tyr Met Ser Trp Val Arg Gln Ala Pro Gly Lys Gly
290                 295                 300

Leu Glu Trp Val Ser Val Ile Tyr Ser Gly Ser Thr Tyr Tyr Ala
305                 310                 315                 320

Asp Ser Val Lys Gly Arg Phe Thr Ile Ser Arg Asp Asn Ser Lys Asn
                325                 330                 335

Thr Leu Tyr Leu Gln Met Asn Ser Leu Arg Ala Glu Asp Thr Ala Val
            340                 345                 350

Tyr Tyr Cys Ala Arg Gly Ile Ala Ala Gly Leu Asp Tyr Trp Gly
        355                 360                 365

Gln Gly Thr Leu Val Thr Val Ser Ser Ala Ser Thr Lys Gly Pro Ser
    370                 375                 380

Val Phe Pro Leu Ala Pro Ser Ser Lys Ser Thr Ser Gly Gly Thr Ala
385                 390                 395                 400

Ala Leu Gly Cys Leu Val Lys Asp Tyr Phe Pro Glu Pro Val Thr Val
                405                 410                 415

Ser Trp Asn Ser Gly Ala Leu Thr Ser Gly Val His Thr Phe Pro Ala
            420                 425                 430

Val Leu Gln Ser Ser Gly Leu Tyr Ser Leu Ser Ser Val Val Thr Val
        435                 440                 445

Pro Ser Ser Leu Gly Thr Gln Thr Tyr Ile Cys Asn Val Asn His
    450                 455                 460

Lys Pro Ser Asn Thr Lys Val Asp Lys Val Glu Pro Lys Ser Cys
465                 470                 475                 480

Asp Lys Thr Ser Gly Gln Ala Gly Gln His His His His His Gly
                485                 490                 495

Ala Tyr Pro Tyr Asp Val Pro Asp Tyr Ala Ser
            500                 505

<210> SEQ ID NO 18
<211> LENGTH: 12
<212> TYPE: PRT
<213> ORGANISM: Artificial Sequence
<220> FEATURE:
<223> OTHER INFORMATION: Synthetic

<400> SEQUENCE: 18

Gly Leu Gln Ser Asn Ser Tyr Arg Ser Leu Ile Met
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic

<400> SEQUENCE: 19

Asp Arg Leu Gln Ser Leu Ser Tyr Arg Thr Ala Leu
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic
```

```
<400> SEQUENCE: 20

Thr Asn Gly Pro Trp Pro Gly Ala Met Thr Asn Pro
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic

<400> SEQUENCE: 21

Gly His Tyr Gln Ser Gln Ser Tyr Arg Ser Pro Asp
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic

<400> SEQUENCE: 22

Gly Pro Thr Ala Tyr Ser Tyr Arg Phe Ala Gln Pro
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic

<400> SEQUENCE: 23

Asp Leu Val Ser Ser Ser Tyr Arg Gly Ser Ile Ile
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic

<400> SEQUENCE: 24

Asn Thr Ala Tyr Gln Ser Tyr Ser Tyr Arg Ala Ile
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic

<400> SEQUENCE: 25

Trp Thr Ser Tyr Ser Tyr Arg Val Gly Thr Leu Ala
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic

<400> SEQUENCE: 26
```

```
Asn Pro Leu Val Ser His Ser Tyr Arg Pro Asp Trp
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic

<400> SEQUENCE: 27

Val Pro Trp Gly Leu Ser Tyr Arg Pro Val Gly Ala
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Synthetic

<400> SEQUENCE: 28

Leu Gln Ser Thr Ser Tyr Arg Leu Thr Asn Ser His
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic

<400> SEQUENCE: 29

Ala Thr Ala Pro Thr Ser His Ser Tyr Arg Ser Ile
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthetic

<400> SEQUENCE: 30

Glu Leu Ala Ser His Ala Tyr Arg Thr His Ala Ser
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic

<400> SEQUENCE: 31

Thr His Asn Leu Lys Trp Pro Glu Glu Tyr Tyr Arg
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic

<400> SEQUENCE: 32
```

Thr His Tyr Asn Ser Leu Ala Ser Val Ser Tyr Arg
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic

<400> SEQUENCE: 33

Val Leu Thr Ser Ala Ser Tyr Arg Phe Met Ala Pro
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic

<400> SEQUENCE: 34

Tyr Pro Met Ile Ser Ser Ser Tyr Arg Met Thr Thr
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthetic

<400> SEQUENCE: 35

Gln His His Phe Ile Ser Ser Ser Tyr Arg Pro Ser
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic

<400> SEQUENCE: 36

Asn Met Asn Leu Thr Pro Phe Asp His Trp Asn Asp
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Synthetic

<400> SEQUENCE: 37

Tyr Glu Asp Pro Ser Ser Leu Phe Thr Trp Asn Asp
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Synthetic

<400> SEQUENCE: 38

Ala Asp Thr Ser His Leu Ser Trp Arg Trp Asn Asp

-continued

<210> SEQ ID NO 39
<211> LENGTH: 12
<212> TYPE: PRT
<213> ORGANISM: Artificial Sequence
<220> FEATURE:
<223> OTHER INFORMATION: Synthetic

<400> SEQUENCE: 39

Asn Asp Thr Pro Phe Lys Ala Arg Asn Trp Glu Asp
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Synthetic

<400> SEQUENCE: 40

Tyr Ser Ser Tyr Asn Ser Ser His Leu Trp Thr Asp
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Synthetic

<400> SEQUENCE: 41

Ala Ser Gln Leu Asn Asp Tyr Phe Ser Trp Asn Asp
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Synthetic

<400> SEQUENCE: 42

Thr Pro Ile Tyr Leu Pro Asn Ser Met Trp Asp Asp
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Synthetic

<400> SEQUENCE: 43

Ser His Glu Thr Ser Ile Thr Val Leu Ser Gln Val
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Synthetic

<400> SEQUENCE: 44

Thr Pro Phe Ser Asn His Thr Phe Gly Asp Gly Phe
1               5                   10

```
<210> SEQ ID NO 45
<211> LENGTH: 12
<212> TYPE: PRT
<213> ORGANISM: Artificial Sequence
<220> FEATURE:
<223> OTHER INFORMATION: Synthetic

<400> SEQUENCE: 45

Thr Pro Trp Asn Asn Ser Glu Gln Arg Trp His Asp
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Synthetic

<400> SEQUENCE: 46

Gly Thr Pro Ala Met Leu Lys Met Lys Trp Asp Asp
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Synthetic

<400> SEQUENCE: 47

Asn Pro Glu His Leu Trp His Thr Arg Trp Gly Asp
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Synthetic

<400> SEQUENCE: 48

Asp Gln Gln Leu Ile His Ser Ala Gly Trp Ser Asp
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Synthetic

<400> SEQUENCE: 49

Ile Thr Thr Lys Ala Tyr Asn Ile Lys Trp Ser Asp
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Synthetic

<400> SEQUENCE: 50

Thr Thr Asn Asn Met Asn Ile Thr Ser Trp Glu Asp
1               5                   10
```

<210> SEQ ID NO 51
<211> LENGTH: 12
<212> TYPE: PRT
<213> ORGANISM: Artificial Sequence
<220> FEATURE:
<223> OTHER INFORMATION: Synthetic

<400> SEQUENCE: 51

Leu Gly Met Gly Thr Pro Ile His Glu Trp Asn Asp
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic

<400> SEQUENCE: 52

Trp Pro Ala Ser Leu Tyr Ala Ala Glu Trp Glu Asp
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Synthetic

<400> SEQUENCE: 53

Asn Met Asn Leu Thr Pro Tyr Asp His Trp Asn Asp
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic

<400> SEQUENCE: 54

Ser Asn Met Ile Tyr Phe Trp Arg Glu Ile Pro Glu
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Synthetic

<400> SEQUENCE: 55

His Arg Thr Arg Ser Thr Val Arg Ser His Thr Leu
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Synthetic

<400> SEQUENCE: 56

Ile Asp Arg Lys Arg Pro Tyr Ser Arg Asp Asn Leu
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic

<400> SEQUENCE: 57

Glu Leu Ser Val Ile Gln Lys Trp Arg Phe Phe Ser
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthetic

<400> SEQUENCE: 58

Glu Leu Ser Arg Ile Arg Ser Gly Val Phe Cys Arg
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic

<400> SEQUENCE: 59

Ala Glu Thr Val Glu Ser Cys Leu Ala Lys Ser His
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Synthetic

<400> SEQUENCE: 60

Asp Leu Pro Thr Leu Asn Ala Arg Pro Pro Ile Phe
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthetic

<400> SEQUENCE: 61

His Thr Ser Trp Arg His His Pro Thr Leu Pro Ser
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Synthetic

<400> SEQUENCE: 62

Trp His Lys Pro His Ala Arg Pro Ala Leu Asp Leu
1               5                   10

<210> SEQ ID NO 63

```
<211> LENGTH: 12
<212> TYPE: PRT
<213> ORGANISM: Artificial Sequence
<220> FEATURE:
<223> OTHER INFORMATION: Synthetic

<400> SEQUENCE: 63

Gly His Gly Tyr Trp Ala Ser Lys Phe Trp Gln Lys
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Synthetic

<400> SEQUENCE: 64

Gly His Trp Ser Ser Trp His His Gln Lys Arg Pro
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Synthetic

<400> SEQUENCE: 65

His Val Leu His Lys His Gly His Leu Gln Lys Asn
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Synthetic

<400> SEQUENCE: 66

Asn Gln Gly Pro His Leu Ser Ile Pro Ser Thr Ser
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Synthetic

<400> SEQUENCE: 67

Ala Pro Ile Trp His Lys His Arg Pro His His Gln
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Synthetic

<400> SEQUENCE: 68

Phe His Lys His Pro Ser His Met Trp Arg Leu Ser
1               5                   10

<210> SEQ ID NO 69
<211> LENGTH: 12
```

```
<212> TYPE: PRT
<213> ORGANISM: Artificial Sequence
<220> FEATURE:
<223> OTHER INFORMATION: Synthetic

<400> SEQUENCE: 69

Ser Trp Trp His Lys Thr Ser Pro His His His Arg
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Synthetic

<400> SEQUENCE: 70

Asn His Phe Ser Trp Ser Thr Pro Pro Ser Ala Glu
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Synthetic

<400> SEQUENCE: 71

Asn Phe His Tyr Leu Ser His Ala Met Thr Pro Asn
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Synthetic

<400> SEQUENCE: 72

Leu Pro His Val Thr His Arg His His Lys Phe
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Synthetic

<400> SEQUENCE: 73

Ala Tyr Pro Thr Gln Thr Val Ala Arg Ala Met Thr
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Synthetic

<400> SEQUENCE: 74

Gly His Gly Trp Trp Ala Lys His Pro Arg Thr Leu
1               5                   10

<210> SEQ ID NO 75
<211> LENGTH: 12
<212> TYPE: PRT
```

<213> ORGANISM: Artificial Sequence
<220> FEATURE:
<223> OTHER INFORMATION: Synthetic

<400> SEQUENCE: 75

Trp His Lys His Pro Ser Phe Ser Gly Arg His Asn
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Synthetic

<400> SEQUENCE: 76

Ala Pro His His Leu Ser Trp Arg His His His Ser
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Synthetic

<400> SEQUENCE: 77

His Trp Gly Asn His Ser Lys Ser His Pro Gln Arg
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Synthetic

<400> SEQUENCE: 78

Leu His Arg His Pro His Pro His Thr Ile Pro Pro
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Synthetic

<400> SEQUENCE: 79

His Trp Lys Pro Trp Pro Thr Ala Arg Phe Gln Thr
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Synthetic

<400> SEQUENCE: 80

His Gly Met His Lys His Trp Ser Trp Lys Ser Asn
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Synthetic

<400> SEQUENCE: 81

Trp Pro Ser His Arg His Ile His Pro Ala Pro Val
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Synthetic

<400> SEQUENCE: 82

Phe Gly Pro Ser Thr Tyr Pro Trp Thr Leu Tyr Ala
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Synthetic

<400> SEQUENCE: 83

Trp Val Pro His His His His Arg Ala Thr Lys Thr
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Synthetic

<400> SEQUENCE: 84

Lys Asn His Gly Ala Thr Arg Thr Thr Arg Ala Ser
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Synthetic

<400> SEQUENCE: 85

Asp Ser Asn Thr Trp Met Tyr Asn Phe Tyr Ser Tyr
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Synthetic

<400> SEQUENCE: 86

His Lys Thr Asp Ser Gln Lys Val Phe Pro Val Ser
1               5                   10

<210> SEQ ID NO 87
<211> LENGTH: 12
<212> TYPE: PRT
<213> ORGANISM: Artificial Sequence
<220> FEATURE:

<223> OTHER INFORMATION: Synthetic

<400> SEQUENCE: 87

Gly Leu His Lys His His Leu Met His Lys Trp Arg
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Synthetic

<400> SEQUENCE: 88

Phe His Lys Pro Ser Trp His Ala Trp Ser Gly Arg
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Synthetic

<400> SEQUENCE: 89

Lys Leu Trp His His His His Pro Ser Arg Tyr Ile
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Synthetic

<400> SEQUENCE: 90

His His Lys Ser Trp Ile Thr Lys Gly Met Pro Pro
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Synthetic

<400> SEQUENCE: 91

Phe His Lys Pro His Met Pro Phe Gln Ser Asn Arg
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Synthetic

<400> SEQUENCE: 92

Ala His Pro His Phe Lys His Thr His His Arg Pro
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Syhthetic

```
<400> SEQUENCE: 93

Leu Pro Phe His Asn His Lys Tyr Trp Asn Arg Leu
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Synthetic

<400> SEQUENCE: 94

Gln Asn Leu Met Asp Gln Met Pro Pro Pro Val His
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Synthetic

<400> SEQUENCE: 95

His Trp Asp Tyr Val Arg Gln Leu Ser Leu Val Gln
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Synthetic

<400> SEQUENCE: 96

Ser Tyr Leu Gln Ser Lys Ser Tyr Phe Leu Pro Pro
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Synthetic

<400> SEQUENCE: 97

Thr His Val Ser Pro Arg Leu Thr Ala Pro Met Val
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Synthetic

<400> SEQUENCE: 98

His Phe Arg His Met His Gln Val Val Gly Gly Pro
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Synthetic
```

```
<400> SEQUENCE: 99

Ser Pro Leu Thr Val Pro Tyr Glu Arg Lys Leu Leu
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Synthetic

<400> SEQUENCE: 100

Phe Pro Lys Trp Tyr His Gly His Val Asn Arg Ser
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Synthetic

<400> SEQUENCE: 101

Val Glu Ala His Lys Arg Pro Trp Asn Phe Phe Arg
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Synthetic

<400> SEQUENCE: 102

Tyr Met Pro Ala Asn Gln Ser Ala Leu Pro His Arg
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Synthetic

<400> SEQUENCE: 103

Lys Pro Tyr Pro Tyr Pro Ala Ala Arg Ile Leu Pro
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Synthetic

<400> SEQUENCE: 104

His Pro His Lys His Lys Thr His Pro Pro Met Val
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Synthetic

<400> SEQUENCE: 105
```

```
Ser Ser Ile Gln Trp Asn Pro Tyr Phe Thr Pro Lys
1               5                   10
```

<210> SEQ ID NO 106
<211> LENGTH: 12
<212> TYPE: PRT
<213> ORGANISM: Artificial Sequence
<220> FEATURE:
<223> OTHER INFORMATION: Synthetic

<400> SEQUENCE: 106

```
Arg Ile Arg Gln His Lys His Asn Arg Gln Lys Gly
1               5                   10
```

<210> SEQ ID NO 107
<211> LENGTH: 12
<212> TYPE: PRT
<213> ORGANISM: Artificial Sequence
<220> FEATURE:
<223> OTHER INFORMATION: Synthetic

<400> SEQUENCE: 107

```
Trp Pro His His Phe Ser Leu His Trp Arg Asn Pro
1               5                   10
```

<210> SEQ ID NO 108
<211> LENGTH: 12
<212> TYPE: PRT
<213> ORGANISM: Artificial Sequence
<220> FEATURE:
<223> OTHER INFORMATION: Synthetic

<400> SEQUENCE: 108

```
Ser Val His Arg Arg Leu Arg Trp Arg Ala Leu Lys
1               5                   10
```

<210> SEQ ID NO 109
<211> LENGTH: 12
<212> TYPE: PRT
<213> ORGANISM: Artificial Sequence
<220> FEATURE:
<223> OTHER INFORMATION: Synthetic

<400> SEQUENCE: 109

```
Val Ser Arg His Gln Ser Trp His Pro His Asp Leu
1               5                   10
```

<210> SEQ ID NO 110
<211> LENGTH: 12
<212> TYPE: PRT
<213> ORGANISM: Artificial Sequence
<220> FEATURE:
<223> OTHER INFORMATION: Synthetic

<400> SEQUENCE: 110

```
Trp Pro Gly Phe Phe His Ser His Arg Thr Gly Pro
1               5                   10
```

<210> SEQ ID NO 111
<211> LENGTH: 12
<212> TYPE: PRT
<213> ORGANISM: Artificial Sequence
<220> FEATURE:
<223> OTHER INFORMATION: Synthetic

<400> SEQUENCE: 111

Trp His Thr Asn His Lys Gln His Trp Arg His Thr
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Synthetic

<400> SEQUENCE: 112

Trp Pro His His His His Thr Arg Leu Ser Thr Val
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Synthetic

<400> SEQUENCE: 113

Phe Pro Thr Trp Lys Pro Trp His Arg Thr His Leu
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Synthetic

<400> SEQUENCE: 114

Phe His Arg His His Ser Pro Pro Pro Ser Ile Ile
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Synthetic

<400> SEQUENCE: 115

His His Trp Lys Phe Phe Phe Ser His Pro Gly Ala
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Synthetic

<400> SEQUENCE: 116

Phe His Arg His Pro His Pro His Asn Leu Ile Arg
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Synthetic

<400> SEQUENCE: 117

His Ile Ser His Lys Asn Leu His Arg Trp Ile Lys

<210> SEQ ID NO 118
<211> LENGTH: 12
<212> TYPE: PRT
<213> ORGANISM: Artificial Sequence
<220> FEATURE:
<223> OTHER INFORMATION: Synthetic

<400> SEQUENCE: 118

Trp His Lys His Ile Pro Ser Ile Arg Phe Pro Ser
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Synthetic

<400> SEQUENCE: 119

Thr Lys Arg Phe Lys Trp Arg Pro Trp Arg Gly Val
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Synthetic

<400> SEQUENCE: 120

Lys His Leu His Ala Pro Gly Trp Tyr Thr Arg Met
1               5                   10

<210> SEQ ID NO 121
<211> LENGTH: 12
<212> TYPE: PRT
<213> ORGANISM: Artificial Sequence
<220> FEATURE:
<223> OTHER INFORMATION: Synthetic

<400> SEQUENCE: 121

His Trp Trp Lys His Pro Thr Arg Tyr Ser Leu Gly
1               5                   10

<210> SEQ ID NO 122
<211> LENGTH: 12
<212> TYPE: PRT
<213> ORGANISM: Artificial Sequence
<220> FEATURE:
<223> OTHER INFORMATION: Synthetic

<400> SEQUENCE: 122

Ser Ile Val Pro Thr Asn Phe Phe Tyr Pro Pro Val
1               5                   10

<210> SEQ ID NO 123
<211> LENGTH: 12
<212> TYPE: PRT
<213> ORGANISM: Artificial Sequence
<220> FEATURE:
<223> OTHER INFORMATION: Synthetic

<400> SEQUENCE: 123

Gly His Tyr Pro Trp Trp Lys Asn His Met Arg Ser
1               5                   10

<210> SEQ ID NO 124
<211> LENGTH: 12
<212> TYPE: PRT
<213> ORGANISM: Artificial Sequence
<220> FEATURE:
<223> OTHER INFORMATION: Synthetic

<400> SEQUENCE: 124

Trp Pro Gln Thr Ala Thr Arg Thr Ser Leu Leu Ser
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Synthetic

<400> SEQUENCE: 125

Val Pro Asn Lys Leu Ser Ser Ser Tyr Trp His Gln
1               5                   10

<210> SEQ ID NO 126
<211> LENGTH: 12
<212> TYPE: PRT
<213> ORGANISM: Artificial Sequence
<220> FEATURE:
<223> OTHER INFORMATION: Synthetic

<400> SEQUENCE: 126

Phe His Lys His Pro His Ser Gly Arg Trp Tyr Pro
1               5                   10

<210> SEQ ID NO 127
<211> LENGTH: 12
<212> TYPE: PRT
<213> ORGANISM: Artificial Sequence
<220> FEATURE:
<223> OTHER INFORMATION: Synthetic

<400> SEQUENCE: 127

Gly Tyr Phe Pro His Trp His Lys Arg Thr Pro Gly
1               5                   10

<210> SEQ ID NO 128
<211> LENGTH: 12
<212> TYPE: PRT
<213> ORGANISM: Artificial Sequence
<220> FEATURE:
<223> OTHER INFORMATION: Synthetic

<400> SEQUENCE: 128

Tyr Asn Ser Thr Ile Arg Ile Val Ser Thr Glu Ile
1               5                   10

<210> SEQ ID NO 129
<211> LENGTH: 12
<212> TYPE: PRT
<213> ORGANISM: Artificial Sequence
<220> FEATURE:
<223> OTHER INFORMATION: Synthetic

<400> SEQUENCE: 129

Ser Pro Lys Gln Pro Leu Thr Gly Pro Leu Val Phe
1               5                   10

```
<210> SEQ ID NO 130
<211> LENGTH: 12
<212> TYPE: PRT
<213> ORGANISM: Artificial Sequence
<220> FEATURE:
<223> OTHER INFORMATION: Synthetic

<400> SEQUENCE: 130

Ala Lys Leu Pro Trp His His His His Gly Arg Pro
1               5                   10

<210> SEQ ID NO 131
<211> LENGTH: 12
<212> TYPE: PRT
<213> ORGANISM: Artificial Sequence
<220> FEATURE:
<223> OTHER INFORMATION: Synthetic

<400> SEQUENCE: 131

Lys Pro Pro Gln Asn Thr Ser Ala Pro Tyr Leu Pro
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Synthetic

<400> SEQUENCE: 132

His Pro Arg Ala Ala Pro Leu Ala Tyr Arg Ser Ala
1               5                   10

<210> SEQ ID NO 133
<211> LENGTH: 12
<212> TYPE: PRT
<213> ORGANISM: Artificial Sequence
<220> FEATURE:
<223> OTHER INFORMATION: Synthetic

<400> SEQUENCE: 133

Asp His Val Arg Glu Thr Asn Asp Arg Thr Thr Ser
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Synthetic

<400> SEQUENCE: 134

Ser Thr Ser Ser Ile Ser His Gly Ser Asn Gly Arg
1               5                   10

<210> SEQ ID NO 135
<211> LENGTH: 12
<212> TYPE: PRT
<213> ORGANISM: Artificial Sequence
<220> FEATURE:
<223> OTHER INFORMATION: Synthetic

<400> SEQUENCE: 135

Glu Asp Val Leu Arg Trp His Pro Glu Trp Pro Gly
1               5                   10
```

```
<210> SEQ ID NO 136
<211> LENGTH: 12
<212> TYPE: PRT
<213> ORGANISM: Artificial Sequence
<220> FEATURE:
<223> OTHER INFORMATION: Synthetic

<400> SEQUENCE: 136

Thr Pro Pro Trp Ala His Ser Arg Gln Asn Met Tyr
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Synthetic

<400> SEQUENCE: 137

Ile Gln Lys Glu Phe Leu His Lys Pro His Ser Leu
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Synthetic

<400> SEQUENCE: 138

His Glu Thr His Ala Leu Ser Leu Glu Asn Arg Arg
1               5                   10

<210> SEQ ID NO 139
<211> LENGTH: 12
<212> TYPE: PRT
<213> ORGANISM: Artificial Sequence
<220> FEATURE:
<223> OTHER INFORMATION: Synthetic

<400> SEQUENCE: 139

Gly Ala Ala Asp Leu Ala Asn Thr Thr Leu Arg Arg
1               5                   10

<210> SEQ ID NO 140
<211> LENGTH: 12
<212> TYPE: PRT
<213> ORGANISM: Artificial Sequence
<220> FEATURE:
<223> OTHER INFORMATION: DTPNSFISWHAP

<400> SEQUENCE: 140

Asp Thr Pro Asn Ser Phe Ile Ser Trp His Ala Pro
1               5                   10

<210> SEQ ID NO 141
<211> LENGTH: 12
<212> TYPE: PRT
<213> ORGANISM: Artificial Sequence
<220> FEATURE:
<223> OTHER INFORMATION: Synthetic

<400> SEQUENCE: 141

His Gln Val His Met Pro Thr Ile Ala Val Phe Ser
1               5                   10

<210> SEQ ID NO 142
```

```
<211> LENGTH: 12
<212> TYPE: PRT
<213> ORGANISM: Artificial Sequence
<220> FEATURE:
<223> OTHER INFORMATION: Synthetic

<400> SEQUENCE: 142

Ala His Thr Thr Asn Met Leu Leu Leu Arg Thr Thr
1               5                   10

<210> SEQ ID NO 143
<211> LENGTH: 12
<212> TYPE: PRT
<213> ORGANISM: Artificial Sequence
<220> FEATURE:
<223> OTHER INFORMATION: Synthetic

<400> SEQUENCE: 143

His Thr Ser Tyr Phe Gln Tyr Tyr Ala Glu Thr Pro
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Synthetic

<400> SEQUENCE: 144

Ser Ile Pro Lys His Trp Ser Ala Thr Asp Glu Ser
1               5                   10

<210> SEQ ID NO 145
<211> LENGTH: 12
<212> TYPE: PRT
<213> ORGANISM: Artificial Sequence
<220> FEATURE:
<223> OTHER INFORMATION: Synthetic

<400> SEQUENCE: 145

Lys His His His Tyr Phe His His Ala Gly Leu Arg
1               5                   10

<210> SEQ ID NO 146
<211> LENGTH: 12
<212> TYPE: PRT
<213> ORGANISM: Artificial Sequence
<220> FEATURE:
<223> OTHER INFORMATION: Synthetic

<400> SEQUENCE: 146

Ile Pro Met Lys Pro Asp Asp Lys Ser Leu Ala Gln
1               5                   10

<210> SEQ ID NO 147
<211> LENGTH: 12
<212> TYPE: PRT
<213> ORGANISM: Artificial Sequence
<220> FEATURE:
<223> OTHER INFORMATION: Synthetic

<400> SEQUENCE: 147

His Gln Met Pro Ser Pro Leu Pro Glu Arg Gln Leu
1               5                   10

<210> SEQ ID NO 148
<211> LENGTH: 12
```

```
<212> TYPE: PRT
<213> ORGANISM: Artificial Sequence
<220> FEATURE:
<223> OTHER INFORMATION: Synthetic

<400> SEQUENCE: 148

Thr Val Ala Asn Thr Leu Met Thr Pro Pro Leu Pro
1               5                   10

<210> SEQ ID NO 149
<211> LENGTH: 12
<212> TYPE: PRT
<213> ORGANISM: Artificial Sequence
<220> FEATURE:
<223> OTHER INFORMATION: Synthetic

<400> SEQUENCE: 149

Tyr Pro Leu His Ser Gln Gly Ser Lys Glu Gly Gln
1               5                   10

<210> SEQ ID NO 150
<211> LENGTH: 12
<212> TYPE: PRT
<213> ORGANISM: Artificial Sequence
<220> FEATURE:
<223> OTHER INFORMATION: Synthetic

<400> SEQUENCE: 150

Gly Leu Tyr His Glu Gln Val Ser Lys Pro Asn Thr
1               5                   10

<210> SEQ ID NO 151
<211> LENGTH: 12
<212> TYPE: PRT
<213> ORGANISM: Artificial Sequence
<220> FEATURE:
<223> OTHER INFORMATION: Synthetic

<400> SEQUENCE: 151

Asn Thr Asp Asn Arg Pro Asp Val Pro Gly Asn Phe
1               5                   10

<210> SEQ ID NO 152
<211> LENGTH: 12
<212> TYPE: PRT
<213> ORGANISM: Artificial Sequence
<220> FEATURE:
<223> OTHER INFORMATION: Synthetic

<400> SEQUENCE: 152

Gly Asp Arg Trp Glu Arg Val Ser Val Thr Lys Leu
1               5                   10

<210> SEQ ID NO 153
<211> LENGTH: 12
<212> TYPE: PRT
<213> ORGANISM: Artificial Sequence
<220> FEATURE:
<223> OTHER INFORMATION: Synthetic

<400> SEQUENCE: 153

His Met Pro Leu Ile Arg Gln Pro Tyr Trp Asn Asp
1               5                   10

<210> SEQ ID NO 154
<211> LENGTH: 12
<212> TYPE: PRT
```

<213> ORGANISM: Artificial Sequence
<220> FEATURE:
<223> OTHER INFORMATION: Synthetic

<400> SEQUENCE: 154

Gly Thr Ser Thr Phe Asn Ser Val Pro Val Arg Asp
1               5                   10

<210> SEQ ID NO 155
<211> LENGTH: 12
<212> TYPE: PRT
<213> ORGANISM: Artificial Sequence
<220> FEATURE:
<223> OTHER INFORMATION: Synthetic

<400> SEQUENCE: 155

Met Pro Lys Pro Met Ile Ser Asp His Leu Arg Tyr
1               5                   10

<210> SEQ ID NO 156
<211> LENGTH: 12
<212> TYPE: PRT
<213> ORGANISM: Artificial Sequence
<220> FEATURE:
<223> OTHER INFORMATION: Synthetic

<400> SEQUENCE: 156

Ser Ser Tyr Asp Trp Lys Ala Gln Pro Arg Ala Ser
1               5                   10

<210> SEQ ID NO 157
<211> LENGTH: 12
<212> TYPE: PRT
<213> ORGANISM: Artificial Sequence
<220> FEATURE:
<223> OTHER INFORMATION: Synthetic

<400> SEQUENCE: 157

Leu Pro His Pro Leu Ser Ser Ile Glu Trp His Asp
1               5                   10

<210> SEQ ID NO 158
<211> LENGTH: 12
<212> TYPE: PRT
<213> ORGANISM: Artificial Sequence
<220> FEATURE:
<223> OTHER INFORMATION: Synthetic

<400> SEQUENCE: 158

Ala Ile Ala His Thr Ser Tyr Ala Ile Thr Thr Pro
1               5                   10

<210> SEQ ID NO 159
<211> LENGTH: 12
<212> TYPE: PRT
<213> ORGANISM: Artificial Sequence
<220> FEATURE:
<223> OTHER INFORMATION: Synthetic

<400> SEQUENCE: 159

Thr Thr Val Ser Phe Ser Leu Ala Arg Asp His Leu
1               5                   10

<210> SEQ ID NO 160
<211> LENGTH: 12
<212> TYPE: PRT
<213> ORGANISM: Artificial Sequence

```
<220> FEATURE:
<223> OTHER INFORMATION: Synthetic

<400> SEQUENCE: 160

Ser Ile Thr Ile Thr Val Ser His Pro Pro Ala Pro
1               5                   10

<210> SEQ ID NO 161
<211> LENGTH: 12
<212> TYPE: PRT
<213> ORGANISM: Artificial Sequence
<220> FEATURE:
<223> OTHER INFORMATION: Synthetic

<400> SEQUENCE: 161

Glu Trp Thr Arg Val Tyr Ala Pro Phe Asn Gly Tyr
1               5                   10

<210> SEQ ID NO 162
<211> LENGTH: 12
<212> TYPE: PRT
<213> ORGANISM: Artificial Sequence
<220> FEATURE:
<223> OTHER INFORMATION: Synthetic

<400> SEQUENCE: 162

Ala Ala Trp Asn Asp Arg Leu Ile Ala Thr Val Glu
1               5                   10

<210> SEQ ID NO 163
<211> LENGTH: 12
<212> TYPE: PRT
<213> ORGANISM: Artificial Sequence
<220> FEATURE:
<223> OTHER INFORMATION: Synthetic

<400> SEQUENCE: 163

Ser Gly His Gln Leu Leu Leu Asn Lys Met Pro Asn
1               5                   10

<210> SEQ ID NO 164
<211> LENGTH: 12
<212> TYPE: PRT
<213> ORGANISM: Artificial Sequence
<220> FEATURE:
<223> OTHER INFORMATION: Synthetic

<400> SEQUENCE: 164

Val Tyr Ala Asp Val Leu Thr Tyr Gly Ser Ser Phe
1               5                   10

<210> SEQ ID NO 165
<211> LENGTH: 12
<212> TYPE: PRT
<213> ORGANISM: Artificial Sequence
<220> FEATURE:
<223> OTHER INFORMATION: Synthetic

<400> SEQUENCE: 165

Gln Arg Pro Ala Asp Met Gly Thr Gly Ala Leu Lys
1               5                   10

<210> SEQ ID NO 166
<211> LENGTH: 12
<212> TYPE: PRT
<213> ORGANISM: Artificial Sequence
<220> FEATURE:
```

```
<223> OTHER INFORMATION: Synthetic

<400> SEQUENCE: 166

Met Val His Gln Arg His His Tyr Leu Leu Ser Gln
1               5                   10

<210> SEQ ID NO 167
<211> LENGTH: 12
<212> TYPE: PRT
<213> ORGANISM: Artificial Sequence
<220> FEATURE:
<223> OTHER INFORMATION: Synthetic

<400> SEQUENCE: 167

Trp Ile Pro Pro Gln Trp Ser Arg Leu Ile Glu Pro
1               5                   10

<210> SEQ ID NO 168
<211> LENGTH: 12
<212> TYPE: PRT
<213> ORGANISM: Artificial Sequence
<220> FEATURE:
<223> OTHER INFORMATION: Synthetic

<400> SEQUENCE: 168

Val Leu Glu Leu Gly Val Pro Pro Ser Arg Ala
1               5                   10

<210> SEQ ID NO 169
<211> LENGTH: 12
<212> TYPE: PRT
<213> ORGANISM: Artificial Sequence
<220> FEATURE:
<223> OTHER INFORMATION: Synthetic

<400> SEQUENCE: 169

Gln Pro Arg Pro Ser Ile Ile Ser His Tyr Trp Thr
1               5                   10

<210> SEQ ID NO 170
<211> LENGTH: 12
<212> TYPE: PRT
<213> ORGANISM: Artificial Sequence
<220> FEATURE:
<223> OTHER INFORMATION: Synthetic

<400> SEQUENCE: 170

Gln Phe Asn Thr Arg Asp Gly Ile Tyr Ser Thr His
1               5                   10

<210> SEQ ID NO 171
<211> LENGTH: 12
<212> TYPE: PRT
<213> ORGANISM: Artificial Sequence
<220> FEATURE:
<223> OTHER INFORMATION: Synthetic

<400> SEQUENCE: 171

Met Pro Met Gly Phe Lys Pro Val Lys Phe Arg Ala
1               5                   10

<210> SEQ ID NO 172
<211> LENGTH: 12
<212> TYPE: PRT
<213> ORGANISM: Artificial Sequence
<220> FEATURE:
<223> OTHER INFORMATION: Synthetic
```

```
<400> SEQUENCE: 172

Ser Tyr Thr Thr His Pro Glu Leu Asn Ala Asn Met
1               5                   10

<210> SEQ ID NO 173
<211> LENGTH: 12
<212> TYPE: PRT
<213> ORGANISM: Artificial Sequence
<220> FEATURE:
<223> OTHER INFORMATION: Synthetic

<400> SEQUENCE: 173

Ser Ala His Gly Thr Ser Thr Gly Val Pro Trp Pro
1               5                   10

<210> SEQ ID NO 174
<211> LENGTH: 12
<212> TYPE: PRT
<213> ORGANISM: Artificial Sequence
<220> FEATURE:
<223> OTHER INFORMATION: Synthetic

<400> SEQUENCE: 174

Ala Ser Ser Met His His Asn Tyr Ser Val Asn Leu
1               5                   10

<210> SEQ ID NO 175
<211> LENGTH: 12
<212> TYPE: PRT
<213> ORGANISM: Artificial Sequence
<220> FEATURE:
<223> OTHER INFORMATION: Synthetic

<400> SEQUENCE: 175

Gln Asp Arg Leu Pro Asn Arg Trp His Thr Tyr Ile
1               5                   10

<210> SEQ ID NO 176
<211> LENGTH: 12
<212> TYPE: PRT
<213> ORGANISM: Artificial Sequence
<220> FEATURE:
<223> OTHER INFORMATION: Synthetic

<400> SEQUENCE: 176

His Pro Ser Gln Ser Pro Ser Thr Arg Asp Pro Trp
1               5                   10

<210> SEQ ID NO 177
<211> LENGTH: 12
<212> TYPE: PRT
<213> ORGANISM: Artificial Sequence
<220> FEATURE:
<223> OTHER INFORMATION: Synthetic

<400> SEQUENCE: 177

Ser Ala Gln Phe Ser Leu Leu Lys Phe Pro Val Phe
1               5                   10

<210> SEQ ID NO 178
<211> LENGTH: 12
<212> TYPE: PRT
<213> ORGANISM: Artificial Sequence
<220> FEATURE:
<223> OTHER INFORMATION: Synthetic
```

<400> SEQUENCE: 178

Ile Val Gln Pro Ser Met Arg Ala Trp Asn Tyr Val
1               5                   10

<210> SEQ ID NO 179
<211> LENGTH: 12
<212> TYPE: PRT
<213> ORGANISM: Artificial Sequence
<220> FEATURE:
<223> OTHER INFORMATION: Synthetic

<400> SEQUENCE: 179

Leu Pro Gln Arg Leu Gly Val Gly Glu Lys Asp Tyr
1               5                   10

<210> SEQ ID NO 180
<211> LENGTH: 12
<212> TYPE: PRT
<213> ORGANISM: Artificial Sequence
<220> FEATURE:
<223> OTHER INFORMATION: Synthetic

<400> SEQUENCE: 180

Ala Phe Asp Leu His Met Leu Leu Glu Arg Asp Arg
1               5                   10

<210> SEQ ID NO 181
<211> LENGTH: 12
<212> TYPE: PRT
<213> ORGANISM: Artificial Sequence
<220> FEATURE:
<223> OTHER INFORMATION: Synthetic

<400> SEQUENCE: 181

Val Trp Leu Pro Glu Glu Lys Asp Arg Thr Thr Asp
1               5                   10

<210> SEQ ID NO 182
<211> LENGTH: 12
<212> TYPE: PRT
<213> ORGANISM: Artificial Sequence
<220> FEATURE:
<223> OTHER INFORMATION: Synthetic

<400> SEQUENCE: 182

Tyr Pro Ser Ala Pro Pro Gln Trp Leu Thr Asn Thr
1               5                   10

<210> SEQ ID NO 183
<211> LENGTH: 12
<212> TYPE: PRT
<213> ORGANISM: Artificial Sequence
<220> FEATURE:
<223> OTHER INFORMATION: Synthetic

<400> SEQUENCE: 183

Gln Ser Tyr His Asp Asn Thr Gly Glu Arg Asp Pro
1               5                   10

<210> SEQ ID NO 184
<211> LENGTH: 12
<212> TYPE: PRT
<213> ORGANISM: Artificial Sequence
<220> FEATURE:
<223> OTHER INFORMATION: Synthetic

<400> SEQUENCE: 184

```
Phe Asp Asp Asn Gln Pro Arg Gln Phe Lys Ile Pro
1               5                   10
```

<210> SEQ ID NO 185
<211> LENGTH: 12
<212> TYPE: PRT
<213> ORGANISM: Artificial Sequence
<220> FEATURE:
<223> OTHER INFORMATION: Synthetic

<400> SEQUENCE: 185

```
Asn His Gly Glu Arg Asp Arg Ser Phe Phe Leu Gln
1               5                   10
```

<210> SEQ ID NO 186
<211> LENGTH: 12
<212> TYPE: PRT
<213> ORGANISM: Artificial Sequence
<220> FEATURE:
<223> OTHER INFORMATION: Synthetic

<400> SEQUENCE: 186

```
Asn Thr Arg Leu Thr Thr Ile Thr His Pro Thr Pro
1               5                   10
```

<210> SEQ ID NO 187
<211> LENGTH: 12
<212> TYPE: PRT
<213> ORGANISM: Artificial Sequence
<220> FEATURE:
<223> OTHER INFORMATION: Synthetic

<400> SEQUENCE: 187

```
Leu Pro Ser Pro Ser Pro Pro Arg Ile Leu Gln Pro
1               5                   10
```

<210> SEQ ID NO 188
<211> LENGTH: 12
<212> TYPE: PRT
<213> ORGANISM: Artificial Sequence
<220> FEATURE:
<223> OTHER INFORMATION: Synthetic

<400> SEQUENCE: 188

```
Phe Pro Pro Ser Trp Leu Ala Ala Ser Asn Arg Pro
1               5                   10
```

<210> SEQ ID NO 189
<211> LENGTH: 12
<212> TYPE: PRT
<213> ORGANISM: Artificial Sequence
<220> FEATURE:
<223> OTHER INFORMATION: Synthetic

<400> SEQUENCE: 189

```
Ser Phe Met Met Gln Thr Glu Pro Leu Ala Arg His
1               5                   10
```

<210> SEQ ID NO 190
<211> LENGTH: 12
<212> TYPE: PRT
<213> ORGANISM: Artificial Sequence
<220> FEATURE:
<223> OTHER INFORMATION: Synthetic

<400> SEQUENCE: 190

```
Met Gln Asp Pro Gln Val Gln Arg Arg Ile Leu His
1               5                   10
```

<210> SEQ ID NO 191
<211> LENGTH: 12
<212> TYPE: PRT
<213> ORGANISM: Artificial Sequence
<220> FEATURE:
<223> OTHER INFORMATION: Synthetic

<400> SEQUENCE: 191

```
Ala Val Ser Pro Phe Leu Ala Pro Val Asp Leu Pro
1               5                   10
```

<210> SEQ ID NO 192
<211> LENGTH: 12
<212> TYPE: PRT
<213> ORGANISM: Artificial Sequence
<220> FEATURE:
<223> OTHER INFORMATION: Synthetic

<400> SEQUENCE: 192

```
Glu His Ser Thr Tyr Lys Gly Ser Pro Leu Tyr Pro
1               5                   10
```

<210> SEQ ID NO 193
<211> LENGTH: 12
<212> TYPE: PRT
<213> ORGANISM: Artificial Sequence
<220> FEATURE:
<223> OTHER INFORMATION: Synthetic

<400> SEQUENCE: 193

```
Leu Leu Ala Asp Thr Thr His His Arg Pro Trp Thr
1               5                   10
```

<210> SEQ ID NO 194
<211> LENGTH: 12
<212> TYPE: PRT
<213> ORGANISM: Artificial Sequence
<220> FEATURE:
<223> OTHER INFORMATION: Synthetic

<400> SEQUENCE: 194

```
Thr Tyr His Glu Ser Gln Thr Ser Phe Thr Asn Thr
1               5                   10
```

<210> SEQ ID NO 195
<211> LENGTH: 12
<212> TYPE: PRT
<213> ORGANISM: Artificial Sequence
<220> FEATURE:
<223> OTHER INFORMATION: Synthetic

<400> SEQUENCE: 195

```
Asn Thr His Asp Ala Arg Asn Pro Leu Asp Tyr Asn
1               5                   10
```

<210> SEQ ID NO 196
<211> LENGTH: 12
<212> TYPE: PRT
<213> ORGANISM: Artificial Sequence
<220> FEATURE:
<223> OTHER INFORMATION: Synthetic

<400> SEQUENCE: 196

```
Asp Lys Ser Val Ser Pro Leu Leu Val Gly Arg Ala
```

-continued

```
<210> SEQ ID NO 197
<211> LENGTH: 12
<212> TYPE: PRT
<213> ORGANISM: Artificial Sequence
<220> FEATURE:
<223> OTHER INFORMATION: Synthetic

<400> SEQUENCE: 197

Leu Gly Phe Asp Pro Thr Ser Thr Arg Phe Tyr Thr
1               5                   10

<210> SEQ ID NO 198
<211> LENGTH: 12
<212> TYPE: PRT
<213> ORGANISM: Artificial Sequence
<220> FEATURE:
<223> OTHER INFORMATION: Synthetic

<400> SEQUENCE: 198

Ile Ala Arg Ala His Pro Pro Leu Gly Leu Asn Ser
1               5                   10

<210> SEQ ID NO 199
<211> LENGTH: 12
<212> TYPE: PRT
<213> ORGANISM: Artificial Sequence
<220> FEATURE:
<223> OTHER INFORMATION: Synthetic

<400> SEQUENCE: 199

Val Thr Gln Pro Asn Glu Arg Asp Tyr His Arg Ser
1               5                   10

<210> SEQ ID NO 200
<211> LENGTH: 12
<212> TYPE: PRT
<213> ORGANISM: Artificial Sequence
<220> FEATURE:
<223> OTHER INFORMATION: Synthetic

<400> SEQUENCE: 200

Phe Val Ser Val Gly Met Lys Pro Ser Pro Arg Pro
1               5                   10

<210> SEQ ID NO 201
<211> LENGTH: 12
<212> TYPE: PRT
<213> ORGANISM: Artificial Sequence
<220> FEATURE:
<223> OTHER INFORMATION: Synthetic

<400> SEQUENCE: 201

His Val Ile Val Gly Met Lys Tyr Glu Phe Leu Gly
1               5                   10

<210> SEQ ID NO 202
<211> LENGTH: 12
<212> TYPE: PRT
<213> ORGANISM: Artificial Sequence
<220> FEATURE:
<223> OTHER INFORMATION: Synthetic

<400> SEQUENCE: 202

Ala Ser Asn Phe Arg Met Pro Glu Leu Gln Ser Ala
1               5                   10
```

```
<210> SEQ ID NO 203
<211> LENGTH: 12
<212> TYPE: PRT
<213> ORGANISM: Artificial Sequence
<220> FEATURE:
<223> OTHER INFORMATION: Synthetic

<400> SEQUENCE: 203

Ser Ile Leu Ser Thr Met Ser Pro His Gly Ala Thr
1               5                   10

<210> SEQ ID NO 204
<211> LENGTH: 12
<212> TYPE: PRT
<213> ORGANISM: Artificial Sequence
<220> FEATURE:
<223> OTHER INFORMATION: Synthetic

<400> SEQUENCE: 204

His Ser Ile Lys His Thr Asn Ala Phe Gln Ala Pro
1               5                   10

<210> SEQ ID NO 205
<211> LENGTH: 12
<212> TYPE: PRT
<213> ORGANISM: Artificial Sequence
<220> FEATURE:
<223> OTHER INFORMATION: Synthetic

<400> SEQUENCE: 205

Ile Val Val Pro Tyr His Gln Asp Ser Met Lys Pro
1               5                   10
```

SPARC BINDING ANTIBODIES AND USES THEREOF

BACKGROUND OF THE INVENTION

Secreted Protein, Acidic, Rich in Cysteines (SPARC), also known as osteonectin, is a 281 amino acid glycoprotein. SPARC has affinity for a wide variety of ligands including cations (e.g., $Ca^{2+}$, $Cu^{2+}$, $Fe^{2+}$), growth factors (e.g., platelet derived growth factor (PDGF), and vascular endothelial growth factor (VEGF)), extracellular matrix (ECM) proteins (e.g., collagen I-V and collagen IX, vitronectin, and thrombospondin-1), endothelial cells, platelets, albumin, and hydroxyapaptite. SPARC expression is developmentally regulated, and is predominantly expressed in tissues undergoing remodeling during normal development or in response to injury (see, e.g., Lane et al., *FASEB J.*, 8, 163-173 (1994)). High levels of SPARC protein are expressed in developing bones and teeth.

SPARC is a matricellular protein upregulated in several aggressive cancers, but is absent from the vast majority of normal tissues (Porter et al., *J. Histochem. Cytochem.*, 43, 791 (1995) and see below). Indeed, SPARC expression is induced among a variety of tumors (e.g., bladder, liver, ovary, kidney, gut, and breast). In bladder cancer, for example, SPARC expression has been associated with advanced carcinoma. Invasive bladder tumors of stage T2 or greater have been shown to express higher levels of SPARC than bladder tumors of stage T1 (or less superficial tumors), and have poorer prognosis (see, e.g., Yamanaka et al., *J. Urology*, 166, 2495-2499 (2001)). In meningiomas, SPARC expression has been associated with invasive tumors only (see, e.g., Rempel et al., *Clincal Cancer Res.*, 5, 237-241 (1999)). SPARC expression also has been detected in 74.5% of in situ invasive breast carcinoma lesions (see, e.g., Bellahcene, et al., *Am. J. Pathol.*, 146, 95-100 (1995)), and 54.2% of infiltrating ductal carcinoma of the breast (see, e.g., Kim et al., *J. Korean Med. Sci.*, 13, 652-657 (1998)). SPARC expression also has been associated with frequent microcalcification in breast cancer (see, e.g., Bellahcene et al., supra), suggesting that SPARC expression may be responsible for the affinity of breast metastases for the bone. SPARC is also known to bind albumin (see, e.g., Schnitzer, *J. Biol. Chem.*, 269, 6072 (1994)).

Accordingly, there is a need for compositions and methods that take advantage of SPARC's role in disease and, in particular, SPARC's role in some cancers.

BRIEF SUMMARY OF THE INVENTION

In one aspect, the invention provides compositions comprising a SPARC binding antibody, wherein the SPARC binding antibody comprises Imm-2, Imm-3, or a combination thereof.

In another aspect, the invention provides methods of diagnosing or treating a disease, such as cancer, in an animal comprising administering a diagnostically or therapeutically effective amount of a composition comprising a SPARC binding antibody, wherein the SPARC binding antibody comprises Imm-2, Imm-3, or a combination thereof.

In all methods and compositions of the present invention, the SPARC binding antibody can be conjugated to a therapeutic or diagnostic active agent. Suitable animals for administration of the compositions provided by the invention and application of the methods of the invention include, without limitation, human patients.

BRIEF DESCRIPTION OF THE SEVERAL VIEWS OF THE DRAWING(S)

FIG. 1 is a restriction map of pASK84 used for cloning and expression of the Fab regions of Imm-1 through Imm-12

FIG. 2 provides the amino acid sequences of two human anti-SPARC Fab clones Fab 6 and Fab 16 (SEQ ID NOs 15-16).

FIG. 3 is a restriction map of the pBAD vector used for cloning and expression of Fab16.

FIG. 4 provides the amino acid sequences of Fab16 in pBad (SEQ ID NO: 17).

FIG. 5 provides amino acid sequences of framework regions (FWRs) and complementarity determining regions (CDRs) for Imm1 (SEQ ID NOs 1 and 8), Imm2 (SEQ ID NOs 2 and 9), Imm3 (SEQ ID NOs 3 and 10), Imm4 (SEQ ID NOs 4 and 11), Imm6 (SEQ ID NOs 5 and 12), Imm10 (SEQ ID NOs 6 and 13), and Imm12 (SEQ ID NOs 7 and 14).

FIG. 6 provides quantitative ELISA results of 1:1, 1:10, and 1:100 dilutions of Imm1-6 and Imm8-12 supernatants against human SPARC, as well as a control mAb.

FIG. 7 provides quantitative ELISA results of 0.04 µg/mL, 0.2 µg/mL, 1 µg/mL, and 5 µg/mL concentrations of purified Imm1-12 antibodies against human SPARC, as well as positive and negative controls.

FIG. 8 provides quantitative ELISA results comparing the binding of Imm1, Imm 3, Imm4, Imm7, Imm9, and Imm10 antibodies to HTI-SPARC (platelet SPARC) and binding of Imm10, Imm11, Imm 12, and control antibodies to Bio1-SPARC.

FIG. 9 provides quantitative ELISA results of Fab 16 (SEQ ID NO: 20) binding to HTI-SPARC (platelet SPARC) and Bio1-SPARC at various concentrations.

Figure 12:
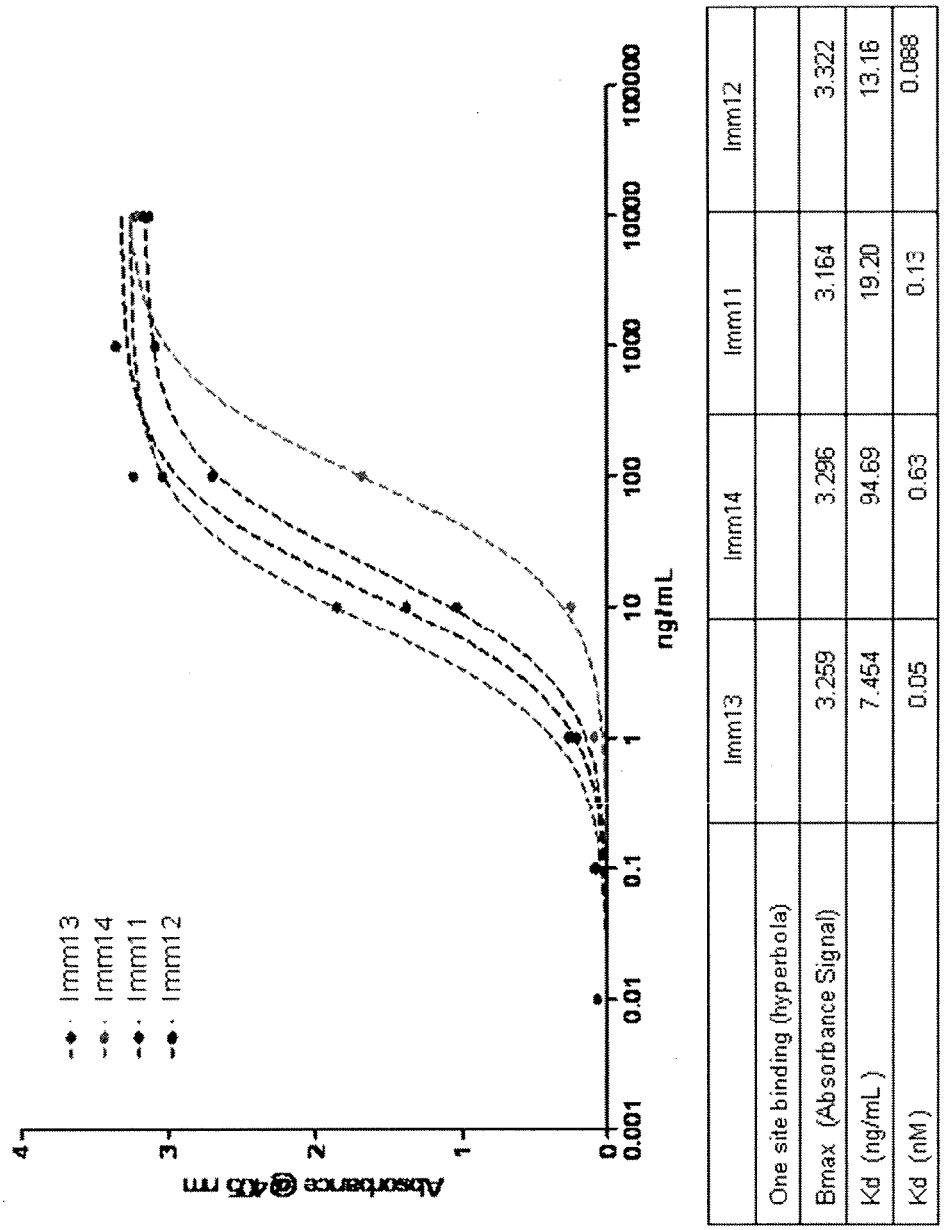

FIG. 12 provides quantitative ELISA results of Imm11, Imm12, Imm13, and Imm14 binding against human SPARC at various concentrations.

Figure 13:
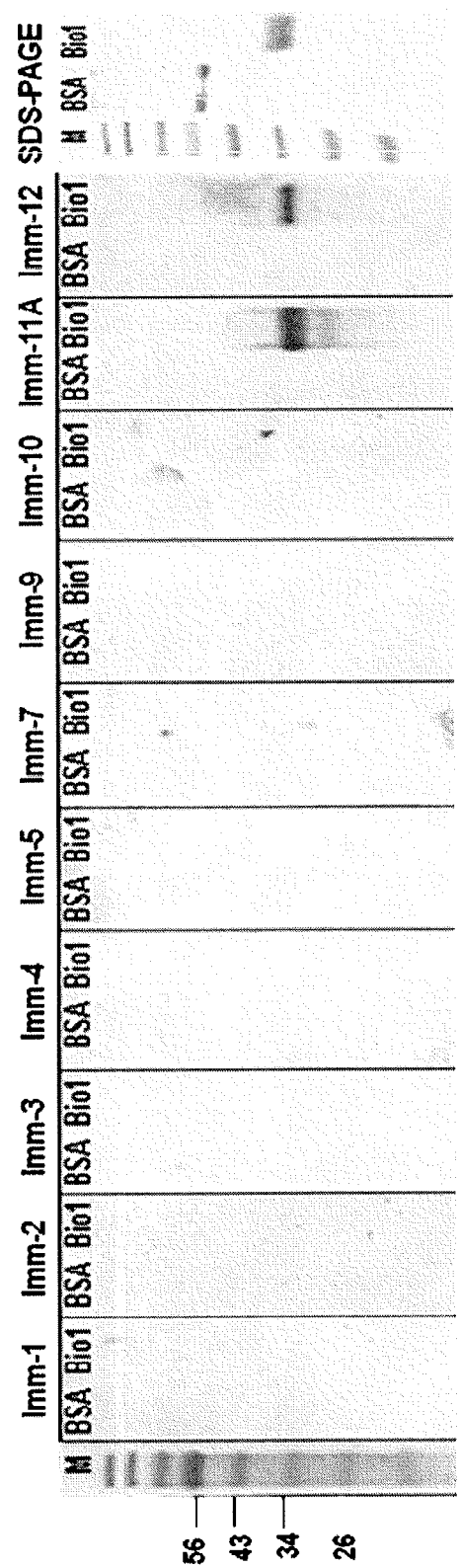

FIG. 13 is a Western Blot of denatured Imm-series antibodies against human SPARC.

Figure 14:
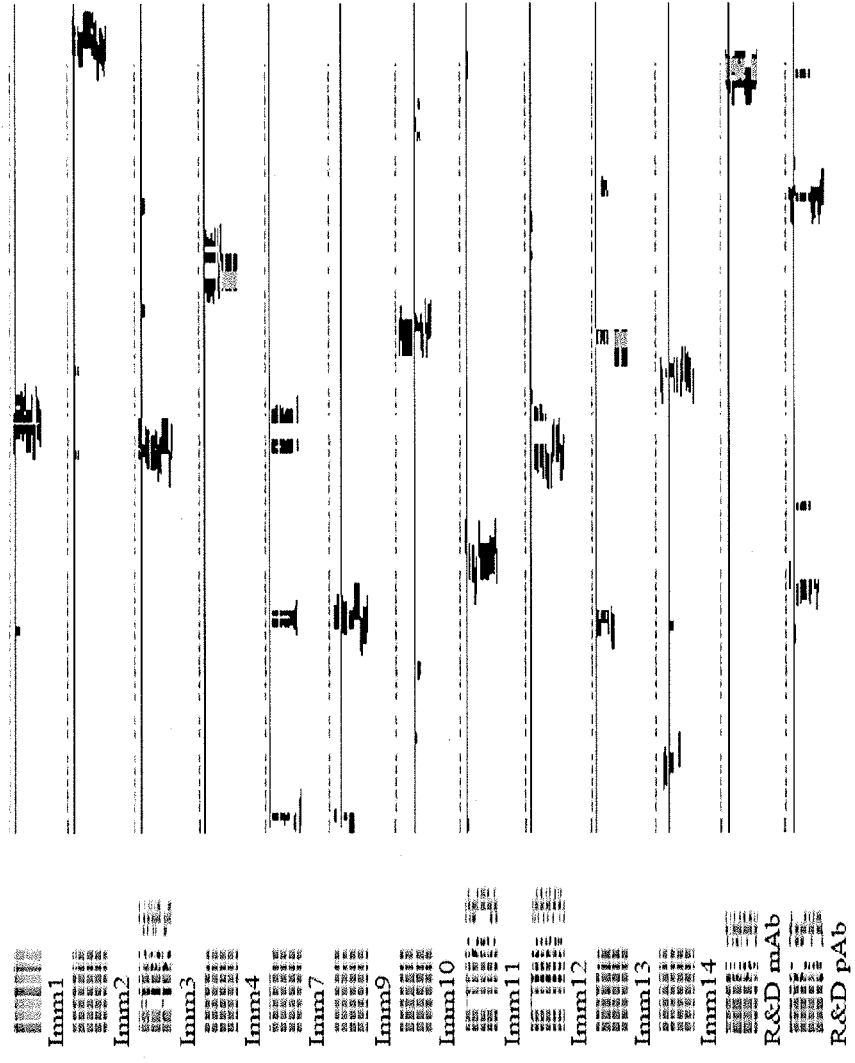

FIG. 14 depicts epitope mapping of Imm1, Imm2, Imm3, Imm4, Imm7, Imm9, Imm10, Imm11, Imm12, Imm13, Imm14, and control mAbs.

FIG. 15 provides peptide sequences from a phage display library against Imm1, Imm2, Imm3, Imm4, Imm7, and control antibodies, aligned against SPARC.

FIG. 16 provides peptide sequences from a phage display library against Imm9, Imm10, Imm11, Imm12, Imm13, and Imm14, aligned against SPARC.

Figure 17:
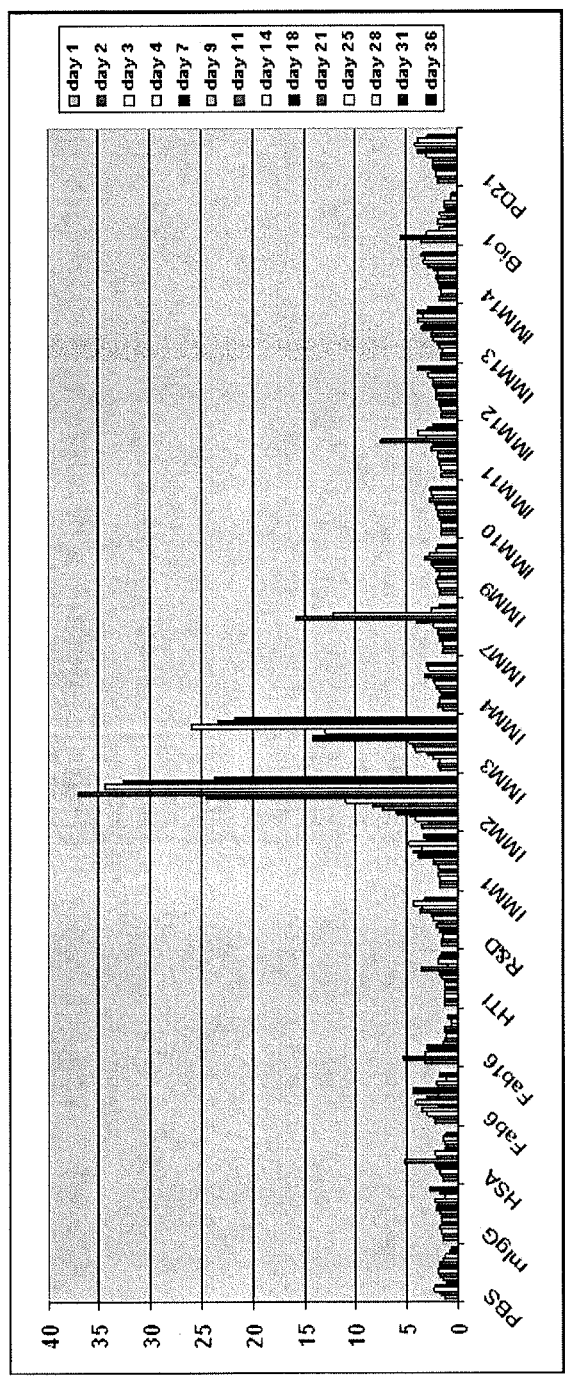

FIG. 17 depicts in vivo tumor localization of Imm1, Imm2, Imm3, Imm4, Imm7, Imm9, Imm10, Imm11, Imm12, Imm13, Imm14, and control antibodies over 36 days.

Figure 18:
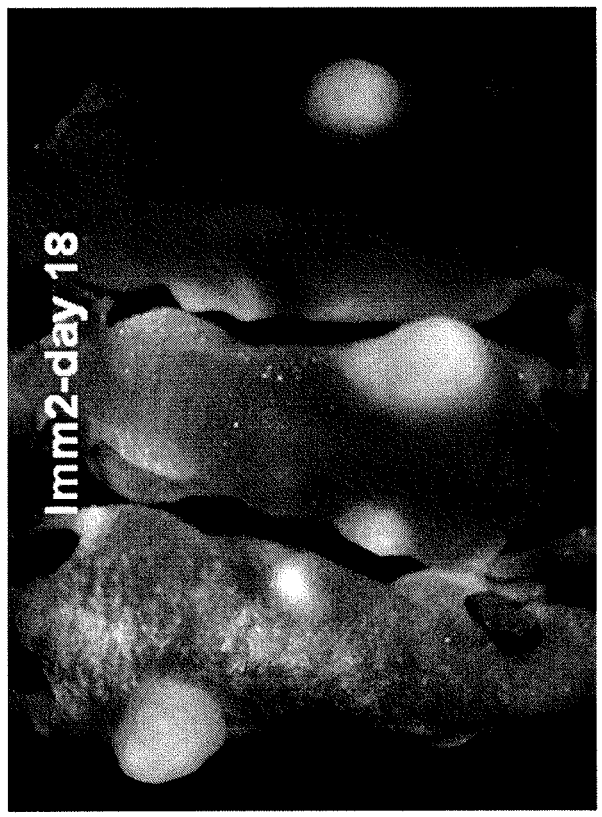

FIG. 18 is a photograph of exemplary nude mice demonstrating visualization of tumors in vivo via Imm2 at day 18.

Figure 19:
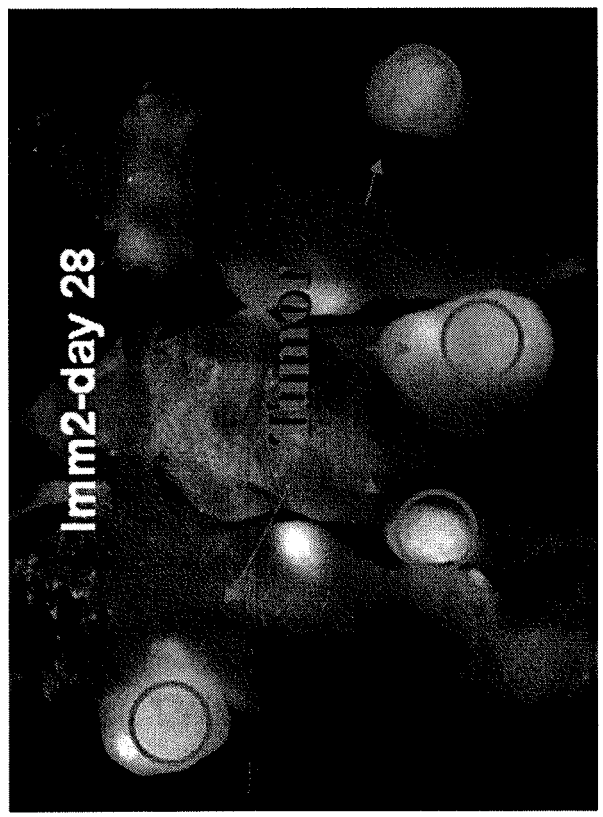

FIG. 19 is a photograph of exemplary nude mice demonstrating visualization of tumors in vivo via Imm2 at day 28.

Figure 20:
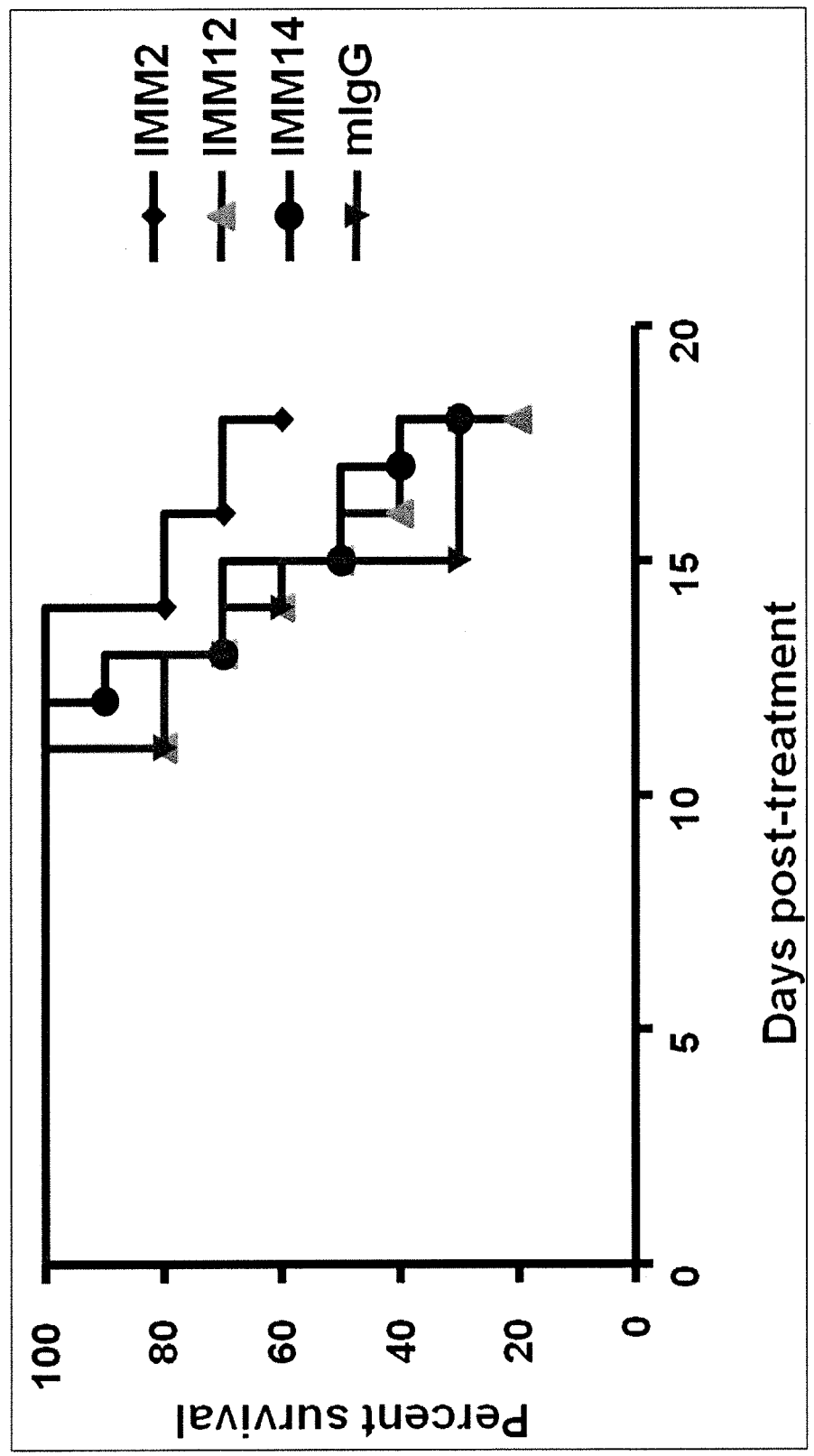

FIG. 20 depicts the effect of anti-SPARC antibodies Imm2, Imm12, and Imm14, as well as control mIgG, on survival of animals bearing LL/2 Lewis Lung Carcinoma.

Figure 21:
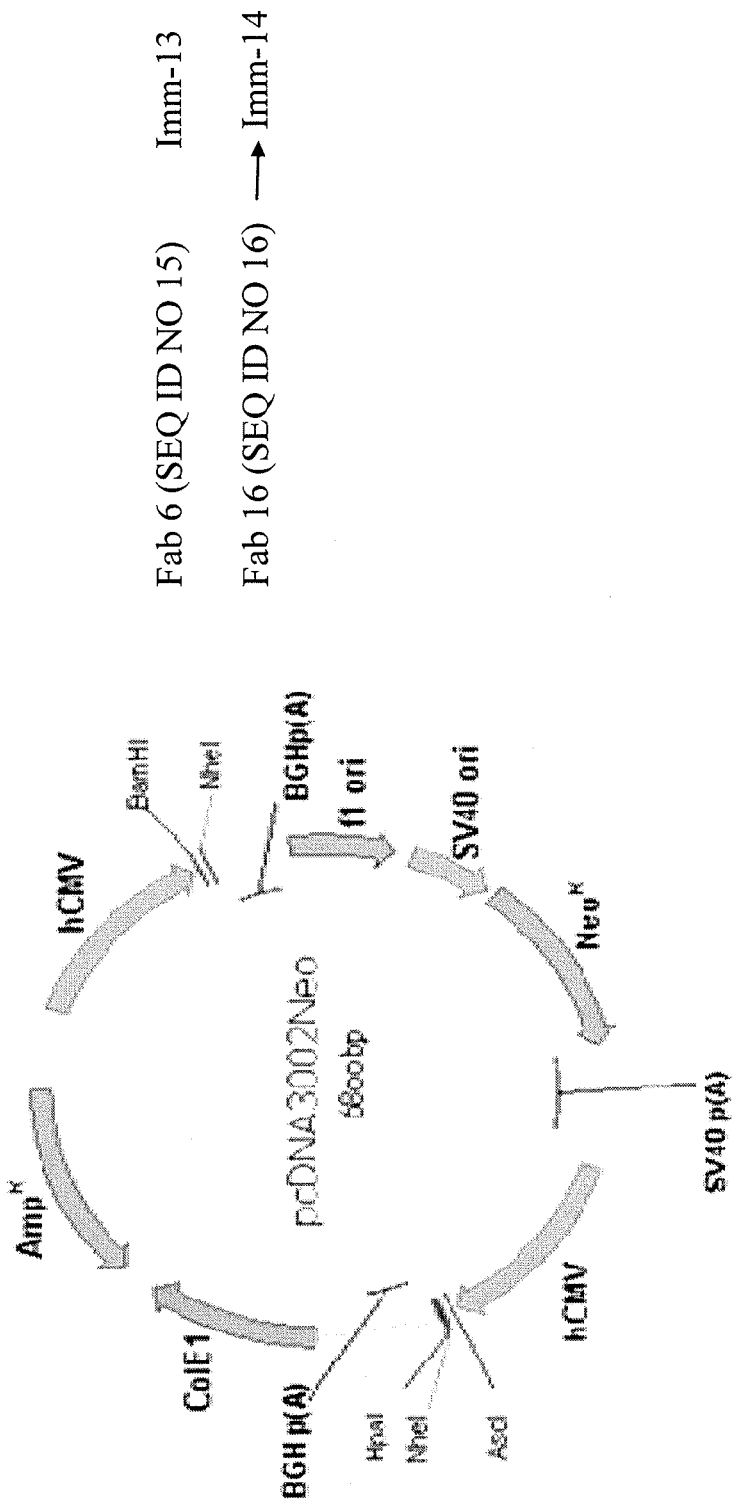

FIG. 21 is a restriction map of the pcDNA3002NEO vector used for the cloning and expression of fully-human antibodies Imm13 and Imm14 from Fab6 (SEQ ID NO: 15) and Fab16 (SEQ ID NO: 16).

DETAILED DESCRIPTION OF THE INVENTION

The present invention relates to the Imm-series of antibodies, a series of 14 SPARC binding antibodies which was analyzed for binding activity and tumor specificity. Surprisingly, the analysis revealed that although all of the antibodies bound SPARC in screening ELISA, two of the antibodies, Imm-2, Imm-3, can be used particularly effectively to target tumors. Without being bound by any particular theories, it is postulated that these two tumor-targeting antibodies are directed to different SPARC epitopes than the other Imm-series antibodies.

DEFINITIONS

"Peptide" and "polypeptide" are used interchangeably herein and refer to a compound made up of a chain of amino acid residues linked by peptide bonds. An "active portion" of a polypeptide means a peptide that is less than the full length polypeptide, but which retains measurable biological activity and retains biological detection.

As used herein, the term "tumor" refers to any neoplastic growth, proliferation or cell mass whether benign or malignant (cancerous), whether a primary site lesion or metastases.

As used herein, the term "cancer" refers to a proliferative disorder caused or characterized by a proliferation of cells which have lost susceptibility to normal growth control. Cancers of the same tissue type usually originate in the same tissue, and may be divided into different subtypes based on their biological characteristics. Four general categories of cancer are carcinoma (epithelial cell derived), sarcoma (connective tissue or mesodermal derived), leukemia (blood-forming tissue derived) and lymphoma (lymph tissue derived). Over 200 different types of cancers are known, and every organ and tissue of the body may be affected. Specific examples of cancers that do not limit the definition of cancer may include melanoma, leukemia, astrocytoma, glioblastoma, retinoblastoma, lymphoma, glioma, Hodgkin's lymphoma, and chronic lymphocytic leukemia. Examples of organs and tissues that may be affected by various cancers include pancreas, breast, thyroid, ovary, uterus, testis, prostate, pituitary gland, adrenal gland, kidney, stomach, esophagus, rectum, small intestine, colon, liver, gall bladder, head and neck, tongue, mouth, eye and orbit, bone, joints, brain, nervous system, skin, blood, nasopharyngeal tissue, lung, larynx, urinary tract, cervix, vagina, exocrine glands, and endocrine glands. Alternatively, a cancer can be multicentric or of unknown primary site (CUPS).

As used herein "a suitable anti-SPARC antibody" or "a SPARC binding antibody" refers to a tumor targeting antibody capable of binding to SPARC with specificity.

As used herein "tumor targeting antibody" refers to a disease targeting antibody wherein the disease is a tumor, cancer, neoplasm or the like.

As used herein "a disease targeting antibody" refers to an antibody that increases the accumulation of an agent at a disease site, in particular, at a tumor site by at least 25%, more preferably at least 50%, even more preferably at least 75%, even more preferably at least 100%, even more preferably at least 3 fold, even more preferably at least 5 fold, even more preferably at least 10 fold, even more preferably at least 20 fold, and most preferably at least 100 fold, as determined by any suitable conventional imaging technique or biopsy and chemical analysis.

As used herein "therapeutically effective amount" refers to an amount of a composition that relieves (to some extent, as judged by a skilled medical practitioner) one or more symptoms of the disease or condition in a mammal. Additionally, by "therapeutically effective amount" of a composition is meant an amount that returns to normal, either partially or completely, physiological or biochemical parameters associated with or causative of a disease or condition. A clinician skilled in the art can determine the therapeutically effective amount of a composition in order to treat or prevent a particular disease condition, or disorder when it is administered, such as intravenously, subcutaneously, intraperitoneally, orally, or through inhalation. The precise amount of the composition required to be therapeutically effective will depend upon numerous factors, e.g., such as the specific activity of the active agent, the delivery device employed, physical characteristics of the agent, purpose for the administration, in addition to many patient specific considerations. But a determination of a therapeutically effective amount is within the skill of an ordinarily skilled clinician upon the appreciation of the disclosure set forth herein.

The terms "treating," "treatment," "therapy," and "therapeutic treatment" as used herein refer to curative therapy, prophylactic therapy, or preventative therapy. An example of "preventative therapy" is the prevention or lessening the chance of a targeted disease (e.g., cancer or other proliferative disease) or related condition thereto. Those in need of treatment include those already with the disease or condition as well as those prone to have the disease or condition to be prevented. The terms "treating," "treatment," "therapy," and "therapeutic treatment" as used herein also describe the management and care of a mammal for the purpose of combating a disease, or related condition, and includes the administration of a composition to alleviate the symptoms, side effects, or other complications of the disease, condition. Therapeutic treatment for cancer includes, but is not limited to, surgery, chemotherapy, radiation therapy, gene therapy, and immunotherapy.

As used herein, the teen "agent" or "drug" or "therapeutic agent" refers to a chemical compound, a mixture of chemical compounds, a biological macromolecule, or an extract made from biological materials such as bacteria, plants, fungi, or animal (particularly mammalian) cells or tissues that are suspected of having therapeutic properties. The agent or drug can be purified, substantially purified or partially purified. An "agent" according to the present invention, also includes a radiation therapy agent or a "chemotherapuetic agent."

As used herein, the term "diagnostic agent" refers to any chemical used in the imaging of diseased tissue, such as, e.g., a tumor.

As used herein, the term "chemotherapuetic agent" refers to an agent with activity against cancer, neoplastic, and/or proliferative diseases.

As used herein, the term "radiotherapeutic regimen" or "radiotherapy" refers to the administration of radiation to kill cancerous cells. Radiation interacts with various molecules within the cell, but the primary target, which results in cell death is the deoxyribonucleic acid (DNA). However, radiotherapy often also results in damage to the cellular and nuclear membranes and other organelles. DNA damage usually involves single and double strand breaks in the sugar-phosphate backbone. Furthermore, there can be cross-linking of DNA and proteins, which can disrupt cell function. Depending on the radiation type, the mechanism of DNA damage may vary as does the relative biologic effectiveness. For example, heavy particles (i.e. protons, neutrons) damage DNA directly and have a greater relative biologic effectiveness. Whereas, electromagnetic radiation results in indirect ionization acting through short-lived, hydroxyl free radicals produced primarily by the ionization of cellular water. Clinical applications of radiation consist of external beam radiation (from an outside source) and brachytherapy (using a source of radiation implanted or inserted into the patient). External beam radiation consists of X-rays and/or gamma rays, while brachytherapy employs radioactive nuclei that decay and emit alpha particles, or beta particles along with a gamma ray.

As used herein the term "alternative therapeutic regimen" or "alternative therapy" (not a first line chemotherapeutic regimen as described above) may include for example, receptor tyrosine kinase inhibitors (for example Iressa™ (gefitinib), Tarceva™ (erlotinib), Erbitux™ (cetuximab), imatinib mesilate (Gleevec™), proteosome inhibitors (for example bortezomib, Velcade™); VEGFR2 inhibitors such as PTK787 (ZK222584), aurora kinase inhibitors (for example ZM447439); mammalian target of rapamycin (mTOR) inhibitors, cyclooxygenase-2 (COX-2) inhibitors, rapamycin inhibitors (for example sirolimus, Rapamune™); farnesyltransferase inhibitors (for example tipifarnib, Zarnestra); matrix metalloproteinase inhibitors (for example BAY 12-9566; sulfated polysaccharide tecogalan); angiogenesis inhibitors (for example Avastin™ (bevacizumab); analogues of fumagillin such as TNP-4; carboxyaminotriazole; BB-94 and BB-2516; thalidomide; interleukin-12; linomide; peptide fragments; and antibodies to vascular growth factors and vascular growth factor receptors); platelet derived growth factor receptor inhibitors, protein kinase C inhibitors, mitogen-activated kinase inhibitors, mitogen-activated protein kinase kinase inhibitors, Rouse sarcoma virus transforming oncogene (SRC) inhibitors, histonedeacetylase inhibitors, small hypoxia-inducible factor inhibitors, hedgehog inhibitors, and TGF-β signalling inhibitors. Furthermore, an immunotherapeutic agent would also be considered an alternative therapeutic regimen. For example, serum or gamma globulin containing preformed antibodies; nonspecific immunostimulating adjuvants; active specific immunotherapy; and adoptive immunotherapy. In addition, alternative therapies may include other biological-based chemical entities such as polynucleotides, including antisense molecules, polypeptides, antibodies, gene therapy vectors and the like. Such alternative therapeutics may be administered alone or in combination, or in combination with other therapeutic regimens described herein. Methods of use of chemotherapeutic agents and other agents used in alternative therapeutic regimens in combination therapies, including dosing and administration regimens, will also be known to a one skilled in the art.

Antibodies

The invention provides a SPARC binding antibody. In particular, the SPARC binding antibody can be Imm-2, Imm-3, or combinations thereof.

In addition, the invention provides for a SPARC binding antibody capable of binding both SPARC found in the blood, e.g. HTI (platelet) SPARC and SPARC found at a tumor site, e.g. Bio1-SPARC. Various methods of determining antibody binding strength are known to those of ordinary skill in the art.

For human use, in order to avoid immunogenicity and immune response, it is preferable to use a humanized SPARC binding antibody or suitable fragments such as Fab', Fab, or Fab2. Humanized antibody or fragments thereof can be produced, for example, using one of the following established methods: 1) a humanized antibody can be constructed using human IgG backbone replacing the variable CDR region with that of an antibody against SPARC, where the heavy and light chain are independently expressed under separate promoters or coexpressed under one promoter with an IRES sequence; 2) a humanized monoclonal antibody can be raised against SPARC using a mouse engineered to have a human immune system; 3) a humanized antibody against SPARC can be raised using phagemid (M13, lambda coliphage, or any phage system capable of surface presentation). To construct the full length antibody, the variable region can be transferred onto the CDR of both a heavy chain and a light chain. The coexpression of the heavy chain and light chain in mammalian cells such as CHO, 293, or human myeloid cells can provide a full length antibody. Similarly, Fab', Fab, or Fab2 fragments and single chain antibodies can be prepared using well established methods.

The SPARC binding antibodies of the present invention include whole antibodies as well as fragments of the antibody retaining the binding site for SPARC (e.g., Fab', Fab and Fab2). The antibody can be any class of antibody, e.g., IgM, IgA, IgG, IgE, IgD, and IgY. The antibody can be, for example, a divalent, monovalent, or chimeric antibody with one valence for SPARC and another for an active agent (such as tTF or ricin A, or another active agent as described herein). The humanized antibody is not limited to IgG. The same technologies can be used to generate all other classes of antibodies such as IgE, IgA, IgD, IgM, each having different antibody-dependent cellular cytotoxicity (ADCC) and complement dependent cytotoxicity (CDC) activities appropriate to particular disease target. Functional fragments of the antibody can be generated by limited proteolysis. These fragments can be monovalent such as Fab' or divalent, such as Fab2. Fragments can also be synthesized as single chain scfv or diabodies in *E. coli*.

Compositions

The invention provides a composition comprising a SPARC binding antibody as described above. In some embodiments, the composition comprises either Imm-2 or Imm-3 along with a suitable carrier. In other embodiments, the composition comprises a combination of Imm-2 and Imm-3 along with a suitable carrier. In preferred embodiments, the composition is a pharmaceutically acceptable composition comprising a SPARC binding antibody and a pharmaceutically acceptable carrier.

The compositions of the present invention can further comprise an active agent. In some embodiments, the active agent is a pharmaceutically active therapeutic agent directly able to exert its pharmacological effect. In other embodiments, the active agent is a diagnostic agent. In preferred embodiments, the active agent is a diagnostic or therapeutic active agent conjugated to a tumor-targeting SPARC binding antibody. It will be understood that some active agents are useful as both diagnostic and therapeutic agents, and therefore such terms are not mutually exclusive.

Compositions of the present invention can be used to enhance delivery of the active agent to a disease site relative to delivery of the active agent alone, or to enhance SPARC clearance resulting in a decrease in blood level of SPARC. In preferred embodiments, the decrease in blood level of SPARC is at least about 10%. In more preferred embodiments, the decrease in blood level of SPARC is at least about 15%, 20%, 25%, 30%, 35%, 40%, 45%, or, most preferably, at least about 50%.

The active agent can be any suitable therapeutic agent or diagnostic agent, such as a chemotherapeutic or anticancer agent. Suitable chemotherapeutic agents or other anticancer agents for use in accordance with the invention include, but are not limited to, tyrosine kinase inhibitors (genistein), biologically active agents (TNF, tTF), radionuclides (131I, 90Y, 111In, 211At, 32P and other known therapeutic radionuclides), adriamycin, ansamycin antibiotics, asparaginase, bleomycin, busulphan, cisplatin, carboplatin, carmustine, capecitabine, chlorambucil, cytarabine, cyclophosphamide, camptothecin, dacarbazine, dactinomycin, daunorubicin, dexrazoxane, docetaxel, doxorubicin, etoposide, epothilones, floxuridine, fludarabine, fluorouracil, gemcitabine, hydroxyurea, idarubicin, ifosfamide, irinotecan, lomustine, mechlorethamine, mercaptopurine, meplhalan, methotrexate, rapamycin (sirolimus) and derivatives, mitomycin, mitotane, mitoxantrone, nitrosurea, paclitaxel, pamidronate, pentostatin, plicamycin, procarbazine, rituximab, streptozocin, teniposide, thioguanine, thiotepa, taxanes, vinblastine, vincristine, vinorelbine, taxol, combretastatins, discodermolides, and transplatinum.

Other suitable chemotherapeutic agents for use in accordance with invention include, without limitation, antimetabolites (e.g., asparaginase), antimitotics (e.g., vinca alkaloids), DNA damaging agents (e.g., cisplatin), proapoptotics (agents which induce programmed-cell-death or apoptosis) (e.g., epipodophylotoxins), differentiation inducing agents (e.g., retinoids), antibiotics (e.g., bleomycin), and hormones (e.g., tamoxifen, diethylstibestrol). Further, suitable chemotherapeutic agents for use in accordance with the invention include antiangiogenesis agents (angiogenesis inhibitors) such as, e.g., INF-alpha, fumagillin, angiostatin, endostatin, thalidomide, and the like.

Preferred chemotherapeutic agents include docetaxel, paclitaxel, and combinations thereof. "Combinations thereof" refers to both the administration of dosage forms including more than one drug, for example, docetaxel and paclitaxel, as well as the sequential but, temporally distinct, administration of docetaxel and paclitaxel (e.g., the use of docetaxel in one cycle and paclitaxel in the next). Particularly preferred chemotherapeutic agents comprise particles of protein-bound drug, including but not limited to, wherein the protein making up the protein-bound drug particles comprises albumin including wherein more than 50% of the chemotherapeutic agent is in nanoparticle form. Most preferably the chemotherapeutic agent comprises particles of albumin-bound paclitaxel, such as, e.g., Abraxane®. Such albumin-bound paclitaxel formulations can be used in accordance with the invention where the paclitaxel dose administered is from about 30 mg/m2 to about 1000 mg/m2 with a dosing cycle of about 3 weeks (i.e., administration of the paclitaxel dose once every about three weeks). Further, it is desirable that the paclitaxel dose administered is from about 50 mg/m2 to about 800 mg/m2, preferably from about 80 mg/m2 to about 700 mg/m2, and most preferably from about 250 mg/m2 to about 300 mg/m2 with a dosing cycle of about 3 weeks.

Other therapeutic agents also include, without limitation, biologically active polypeptides, antibodies and fragments thereof, lectins, and toxins (such as ricin A), or radionuclides. Suitable antibodies for use as active agents in accordance with the invention include, without limitation, conjugated (coupled) or unconjugated (uncoupled) antibodies, monoclonal or polyclonal antibodies, humanized or unhumanized antibodies, as well as Fab', Fab, or Fab2 fragments, single chain antibodies and the like. Contemplated antibodies or antibody fragments can be Fc fragments of IgG, IgA, IgD, IgE, or IgM. In various preferred embodiments, the active agent is the Fc fragment of the antibody itself, a single chain antibody, a Fab fragment, diabody, and the like. In more preferred embodiments, the antibody or antibody fragment mediates complement activation, cell mediated cytotoxicity, and/or opsonization.

In addition, the pharmaceutically active agent can be an siRNA. In preferred embodiments, the siRNA molecule inhibits expression of an gene associated with tumors such as, for example, c-Sis and other growth factors, EGFR, PDGFR, VEGFR, HER2, other receptor tyrosine kinases, Src-family genes, Syk-ZAP-70 family genes, BTK family genes, other cytoplasmic tyrosine kinases, Raf kinase, cyclin dependent kinases, other cytoplasmic serine/threonine kinases, Ras protein and other regulatory GTPases.

The invention further provides a diagnostic agent conjugated to a SPARC binding antibody. Suitable diagnostic agents include, e.g., fluorchromes, radioisotopes or radionuclides, MRI contrast agents, X-ray contrast agents, ultrasound contrast agents and PET contrast agents.

The active agent can be coupled to the tumor-targeting SPARC binding antibody using any method known to one of skill in the art. For example, the SPARC binding antibody and the active agent can be coupled using a method such as biotin-streptavidin conjugation, chemical conjugation, covalent coupling, antibody coupling, and/or direct expression (e.g., a chimeric protein).

In other embodiments, free amino groups in SPARC binding antibodies can be conjugated with reagents such as carbodiimides or heterobiofunctional agents. In addition, sugar moieties bound to suitable SPARC binding antibodies, can be oxidized to form aldehyde groups useful in a number of coupling procedures known in the art. The conjugates formed in accordance with the invention can be stable, in vivo, or labile, such as enzymatically degradeable tetrapeptide linkages, or acid-labile, cis-aconityl, or hydrazone linkages.

SPARC binding antibodies can also be conjugated to polyethylene glycol (PEG). PEG conjugation can increase the circulating half-life of a protein, reduce the protein's immunogenicity and antigenicity, and improve the bioactivity. Any suitable method of conjugation can be used, including but not limited to, e.g., reacting methoxy-PEG with a SPARC binding antibody's available amino groups or other reactive sites such as, e.g., histidines or cysteines. In addition, recombinant DNA approaches can be used to add amino acids with PEG-reactive groups to the inventive SPARC binding antibodies. PEG can be processed prior to reacting it with a SPARC binding antibody, e.g., linker groups can be added to the PEG. Further, releasable and hybrid PEG-ylation strategies can be used in accordance with the invention, such as, e.g., the PEG-ylation of a SPARC binding antibody such that the PEG molecules added to certain sites in the SPARC binding antibody are released in vivo. Such PEG conjugation methods are known in the art (See, e.g., Greenwald et al., Adv. Drug Delivery Rev. 55:217-250 (2003)).

Contemplated SPARC binding antibodies and conjugates thereof can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such as organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

The compositions of the present inventions are generally provided in a formulation with a carrier, such as a pharmaceutically acceptable carrier. Typically, the carrier will be liquid, but also can be solid, or a combination of liquid and solid components. The carrier desirably is a physiologically acceptable (e.g., a pharmaceutically or pharmacologically acceptable) carrier (e.g., excipient or diluent). Suitable pharmaceutical excipients include stabilizers, antioxidants, osmolality adjusting agents, buffers, and pH adjusting agents. Suitable additives include physiologically biocompatible buffers, additions of chelants or calcium chelate complexes, or, optionally, additions of calcium or sodium salts. Pharmaceutical compositions can be packaged for use in liquid form, or can be lyophilized. Preferred physiologically acceptable carrier media are water, buffered water, normal saline, 0.4% saline, 0.3% glycine, hyaluronic acid and the like. Physiologically acceptable carriers are well known and are readily available. The choice of carrier will be determined, at least in part, by the location of the target tissue and/or cells, and the particular method used to administer the composition.

The composition can be formulated for administration by a route including intravenous, intraarterial, intramuscular, intraperitoneal, intrathecal, epidural, topical, percutaneous, subcutaneous, transmucosal (including, for example, pulmonary), intranasal, rectal, vaginal, or oral. The composition also can comprise additional components such as diluents, adjuvants, excipients, preservatives, and pH adjusting agents, and the like.

Formulations suitable for injectable administration include aqueous and nonaqueous, isotonic sterile injection solutions, which can contain anti-oxidants, buffers, bacteriostats, and solutes that render the formulation isotonic with the blood of the intended recipient, and aqueous and nonaqueous sterile suspensions that can include suspending agents, solubilizers, thickening agents, stabilizers, lyoprotectants, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, or tablets.

Sterile injectable solutions can be prepared by incorporating the active compound in the required amount in an appropriate solvent with one or a combination of ingredients enumerated above, as required, followed by filtered sterilization. Preferably solutions for injection are free of endotoxin. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In all cases, the formulation must be sterile and must be fluid to the extent that easy syringability exists. It must be stable under the conditions of manufacture and storage and must be preserved against the contaminating action of microorganisms, such as bacteria and fungi. Solutions of the active compounds as free base or pharmacologically acceptable salts can be prepared in water suitably mixed with a surfactant, such as hydroxycellulose. Dispersions can also be prepared in glycerol, liquid polyethylene glycols, and mixtures thereof and in oils. Under ordinary conditions of storage and use, these preparations contain a preservative to prevent the growth of microorganisms.

In preferred embodiments, the active ingredients can be entrapped in microcapsules prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). Specifically, liposomes containing the SPARC binding antibodies can be prepared by such methods as described in Rezler et al., *J. Am. Chem. Soc.* 129(16): 4961-72 (2007); Samad et al., *Curr. Drug Deliv.* 4(4): 297-305 (2007); and U.S. Pat. Nos. 4,485,045 and 4,544,545. Liposomes with enhanced circulation time are disclosed in U.S. Pat. No. 5,013,556.

Particularly useful liposomes can be generated by, for example, the reverse-phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Polypeptides of the present invention can be conjugated to the liposomes as described in Werle et al., *Int. J. Pharm.* 370(1-2): 26-32 (2009).

In other embodiments, a composition can be delivered using a natural virus or virus-like particle, a dendrimer, carbon nanoassembly, a polymer carrier, a paramagnetic particle, a ferromagnetic particle, a polymersome, a filomicelle, a micelle or a lipoprotein.

Administration into the airways can provide either systemic or local administration, for example to the trachea and/or the lungs. Such administration can be made via inhalation or via physical application, using aerosols, solutions, and devices such as a bronchoscope. For inhalation, the compositions herein are conveniently delivered from an insufflator, a nebulizer, a pump, a pressurized pack, or other convenient means of delivering an aerosol, non-aerosol spray of a powder, or noon-aerosol spray of a liquid. Pressurized packs can comprise a suitable propellant such a liquefied gas or a compressed gas. Liquefied gases include, for example, fluorinated chlorinated hydrocarbons, hydrochlorofluorocarbons, hydrochlorocarbons, hydrocarbons, and hydrocarbon ethers. Compressed gases include, for example, nitrogen, nitrous oxide, and carbon dioxide. In particular, the use of dichlorodifluoromethane, trichlorofluoromethane, dichlorotetrafluoroethane, carbon dioxide or other suitable gas is contemplated. In the case of a pressurized aerosol, the dosage unit can be determined by providing a valve to deliver a controlled amount. In administering a dry powder composition, the powder mix can include a suitable powder base such as lactose or starch. The powder composition can be presented in unit dosage form such as, for example, capsules, cartridges, or blister packs from which the powder can be administered with the aid of an inhaler or insufflator.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays, inhaled aerosols, rectal or vaginal suppositories, mouthwashes, rapidly dissolving tablets, or lozenges. For transdermal administration, the active compounds are formulated into ointments, salves, gels, foams, or creams as generally known in the art.

The pharmaceutical compositions can be delivered using drug delivery systems. Such delivery systems include hyaluronic acid solutions or suspensions of collagen fragments. The drugs can be formulated in microcapsules, designed with appropriate polymeric materials for controlled release, such as polylactic acid, ethylhydroxycellulose, polycaprolactone, polycaprolactone diol, polylysine, polyglycolic, polymaleic acid, poly[N-(2-hydroxypropyl)methylacrylamide] and the like. Particular formulations using drug delivery systems can be in the form of liquid suspensions, ointments, complexes to a bandage, collagen shield or the like.

The composition can further comprise any other suitable components, especially for enhancing the stability of the composition and/or its end-use. Accordingly, there is a wide variety of suitable formulations of the composition of the invention.

Sustained release compositions can also be employed in the present compositions, such as those described in, for example, U.S. Pat. Nos. 5,672,659 and 5,595,760. The use of immediate or sustained release compositions depends on the nature of the condition being treated. If the condition consists of an acute or over-acute disorder, treatment with an immediate release form will be preferred over a prolonged release composition. Alternatively, for certain preventative or long-term treatments, a sustained release composition may be appropriate.

In addition, the composition can comprise additional therapeutic or biologically-active agents. For example, therapeutic factors useful in the treatment of a particular indication can be present. Factors that control inflammation, such as ibuprofen or steroids, can be part of the composition to reduce swelling and inflammation associated with in vivo administration of the pharmaceutical composition and physiological distress.

Compositions provided by the invention can include, e.g., from about 0.5 ml to about 4 ml aqueous or organic liquids with an active agent coupled to a SPARC binding antibody, with the concentration of the active agent from about 10 mg/ml to about 100 mg/ml, preferably from about 1 mg/ml to about 10 mg/ml, more preferably from about 0.1 mg/ml to about 1 mg/ml. The active agent can be present at any suitable and therapeutically effective concentration, e.g., Avastin at a concentration of from about 10 mg/ml to about 50 mg/ml.

Methods

The invention provides a method for diagnosing or treating a disease in an animal by administering a diagnostically or therapeutically effective amount of a composition comprising a SPARC binding antibody comprising Imm-2, Imm-3, or combinations thereof. In some embodiments, the invention provides a method for diagnosing a disease in an animal by administering an effective amount of Imm-2, Imm-3, or a combination thereof. In other embodiments, the invention provides a method for treating a disease in an animal by administering an effective amount of Imm-2, Imm-3, or a combination thereof. Any composition described above can be used in the methods of the present invention.

According to the methods of the present invention, a therapeutically effective amount of the composition can be administered to the mammal to enhance delivery of the active agent to a disease site relative to delivery of the active agent alone, or to enhance clearance resulting in a decrease in blood level of SPARC. In preferred embodiments, the decrease in blood level of SPARC is at least about 10%. In more preferred embodiments, the decrease in blood level of SPARC is at least about 15%, 20%, 25%, 30%, 35%, 40%, 45%, or, most preferably, at least about 50%.

The invention also provides a method of diagnosing a disease or condition in an animal comprising (a) administering to the animal a diagnostically effective amount of a SPARC binding antibody comprising Imm-2, Imm-3, or combinations thereof; (b) detecting the amount of SPARC binding antibody present in a particular site or tissue of the animal; and (c) diagnosing that the disease or condition is present if the amount of SPARC binding antibody present indicates that significantly greater than normal levels of SPARC are present in the particular site or tissue.

The present methods can be used in any condition characterized by overexpression of SPARC. Exemplary diseases for which the present invention is useful include abnormal conditions of proliferation, tissue remodeling, hyperplasia, exaggerated wound healing in any bodily tissue including soft tissue, connective tissue, bone, solid organs, blood vessel and the like. Examples of diseases treatable or diagnosed using the methods and compositions of the present invention include cancer, diabetic or other retinopathy, inflammation, arthritis, restenosis in blood vessels or artificial blood vessel grafts or intravascular devices and the like.

Other diseases within the scope of the methods of the present invention include, without limitation, cancer, restenosis or other proliferative diseases, fibrosis, osteoporosis or exaggerated wound healing. Specifically, such suitable diseases include, without limitation, wherein: (a) the cancer can be, for example, circinoma in situ, atypical hyperplasia, carcinoma, sarcoma, carcinosarcoma, lung cancer, pancreatic cancer, skin cancer, hematological neoplasms, breast cancer, brain cancer, colon cancer, bladder cancer, cervical cancer, endometrial cancer, esophageal cancer, gastric cancer, head and neck cancer, multiple myeloma, liver cancer, leukemia, lymphoma, oral cancer, osteosarcomas, ovarian cancer, prostate cancer, testicular cancer, and thyroid cancer, (b) the restenosis can be, for example, coronary artery restenosis, cerebral artery restenosis, carotid artery restenosis, renal artery restenosis, femoral artery restenosis, peripheral artery restenosis or combinations thereof, (c) the other proliferative disease can be, for example, hyperlasias, endometriosis, hypertrophic scars and keloids, proliferative diabetic retinopathy, glomerulonephritis, proliferative, pulmonary hypertension, rheumatoid arthritis, arteriovenous malformations, atherosclerotic plaques, coronary artery disease, delayed wound healing, hemophilic joints, nonunion fractures, Osler-Weber syndrome, psoriasis, pyogenic granuloma, scleroderma, tracoma, menorrhagia, vascular adhesions, and papillomas, and (d) the fibrotic disease can be, for example, hepatic fibrosis, pulmonary fibrosis and retroperitoneal fibrosis.

The animal can be any patient or subject in need of treatment or diagnosis. In preferred embodiments, the animal is a mammal. In particularly preferred embodiments, the animal is a human. In other embodiments, the animal can be a mouse, rat, rabbit, cat, dog, pig, sheep, horse, cow, or a non-human primate.

The invention also provides a method for destruction of SPARC expression tissues such as tumor and restenotic tissues via the complement fixation and/or recruitment of cell mediated immune response by a SPARC binding antibody.

The invention also provides a method for inhibition of SPARC activity using neutralizing antibody against SPARC, e.g., a suitable anti-SPARC antibody. A neutralizing antibody has the ability to block the interaction of SPARC with its effectors in vivo, for example, the interaction of SPARC with cell surface component or the binding of SPARC to its natural ligands such as albumin, growth factors, and Ca2+. The invention provides a method for delivering a chemotherapeutic agent to a tumor in a mammal. The methods comprise administering to a human or other animal a therapeutically effective amount of a pharmaceutical composition, wherein the pharmaceutical composition comprises the chemotherapeutic agent coupled to a suitable SPARC binding antibody and a pharmaceutically acceptable carrier. Descriptions of the chemotherapeutic agents, animals, and components thereof, set forth herein in connection with other embodiments of the invention also are applicable to those same aspects of the aforesaid method of delivering a chemotherapeutic agent to a tumor.

The types of tumor to be detected, whose response to chemotherapy can be predicted or determined, which can be treated in accordance with the invention are generally those found in humans and other mammals. The tumors can be the result of inoculation as well, such as in laboratory animals. Many types and forms of tumors are encountered in human and other animal conditions, and there is no intention to limit the application of the methods of the present to any particular tumor type or variety. Tumors, as is known, include an abnormal mass of tissue that results from uncontrolled and progressive cell division, and is also typically known as a "neoplasm." The inventive methods are useful for tumor cells and associated stromal cells, solid tumors and tumors associated with soft tissue, such as, soft tissue sarcoma, for example, in a human.

The tumor or cancer can be located in the oral cavity and pharynx, the digestive system, the respiratory system, bones and joints (e.g., bony metastases), soft tissue, the skin (e.g., melanoma), breast, the genital system, the urinary system, the eye and orbit, the brain and central nervous system (e.g., glioma), or the endocrine system (e.g., thyroid) and is not necessarily limited to the primary tumor or cancer. Tissues associated with the oral cavity include, but are not limited to, the tongue and tissues of the mouth. Cancer can arise in tissues of the digestive system including, for example, the esophagus, stomach, small intestine, colon, rectum, anus, liver, gall bladder, and pancreas. Cancers of the respiratory system can affect the larynx, lung, and bronchus and include, for example, small cell and non-small cell lung carcinoma. Tumors can arise in the uterine cervix, uterine corpus, ovary vulva, vagina, prostate, testis, and penis, which make up the male and female genital systems, and the urinary bladder, kidney, renal pelvis, and ureter, which comprise the urinary system. The tumor or cancer can be located in the head and/or neck (e.g., laryngeal cancer and parathyroid cancer). The tumor or cancer also can be located in the hematopoietic system or lymphoid system, and include, for example, lymphoma (e.g., Hodgkin's disease and Non-Hodgkin's lymphoma), multiple myeloma, or leukemia (e.g., acute lymphocytic leukemia, chronic lymphocytic leukemia, acute myeloid leukemia, chronic myeloid leukemia, and the like). Preferably, the tumor is located in the bladder, liver, ovary, kidney, gut, brain, or breast.

In other embodiments, the invention provide a methods for delivering a pharmaceutically active agent by way of a SPARC binding antibody to a site of disease that is characterized by overexpression of SPARC. Such diseases include abnormal conditions of proliferation, tissue remodeling, hyperplasia, and exaggerated wound healing in bodily tissue (e.g., soft tissue, connective tissue, bone, solid organs, blood vessel and the like). Examples of diseases that are treatable or can be diagnosed by administering a pharmaceutical composition comprising a therapeutic agent coupled to a suitable SPARC antibody, include cancer, diabetic or other retinopathy, inflammation, arthritis, restenosis in blood vessels, artificial blood vessel grafts, or intravascular devices, and the like. Descriptions of the chemotherapeutic agents, tumors, animals, and components thereof, set forth herein in connection with other embodiments of the invention also are applicable to those same aspects of the aforesaid method of delivering a pharmaceutically active agent.

In other embodiments, the inventive methods comprise administering to a mammal a therapeutically effective amount of a pharmaceutical composition comprising a liposome bound or albumin bound chemotherapeutic agent wherein the liposome or albumin is coupled to a suitable disease targeting SPARC binding antibody. The chemotherapeutic agent can be coupled to the SPARC binding antibody using any suitable method. Preferably, the chemotherapeutic agent is chemically coupled to the compound via covalent bonds including, for example, disulfide bonds.

One or more doses of one or more chemotherapeutic agents, such as those described above, can also be administered according to the inventive methods. The type and number of chemotherapeutic agents used in the inventive method will depend on the standard chemotherapeutic regimen for a particular tumor type. In other words, while a particular cancer can be treated routinely with a single chemotherapeutic agent, another can be treated routinely with a combination of chemotherapeutic agents. Methods for coupling or conjugation of suitable therapeutics, chemotherapeutics, radionuclides, etc. to antibodies or fragments thereof are well described in the art. The following examples further illustrate the invention but, of course, should not be construed as in any way limiting its scope.

Methods in accordance with the invention include, e.g., combination therapies wherein the animal is also undergoing one or more cancer therapies selected from the group consisting of surgery, chemotherapy, radiotherapy, thermotherapy, immunotherapy, hormone therapy and laser therapy. The terms "co-administration" and "combination therapy" refer to administering to a subject two or more therapeutically active agents. The agents can be contained in a single pharmaceutical composition and be administered at the same time, or the agents can be contained in separate formulation and administered serially to a subject. So long as the two agents can be detected in the subject at the same time, the two agents are said to be co-administered.

Combination therapies contemplated in the present invention include, but are not limited to antibody administration, vaccine administration, administration of cytotoxic agents, natural amino acid polypeptides, nucleic acids, nucleotide analogues, and biologic response modifiers. Two or more combined compounds may be used together or sequentially. Examples of chemotherapeutic agents include alkylating agents, antimetabolites, natural products, hormones and antagonists, and miscellaneous agents. Examples of alkylating agents include nitrogen mustards such as mechlorethamine, cyclophosphamide, ifosfamide, melphalan (L-sarcolysin) and chlorambucil; ethylenimines and methylmelamines such as hexamethylmelamine and thiotepa; alkyl sulfonates such as busulfan; nitrosoureas such as carmustine (BCNU), semustine (methyl-CCNU), lomustine (CCNU) and streptozocin (streptozotocin); DNA synthesis antagonists such as estramustine phosphate; and triazines such as dacarbazine (DTIC, dimethyl-triazenoimidazolecarboxamide) and temozolomide. Examples of antimetabolites include folic acid analogs such as methotrexate (amethopterin); pyrimidine analogs such as fluorouracin (5-fluorouracil, 5-FU, 5FU), floxuridine (fluorodeoxyuridine, FUdR), cytarabine (cytosine arabinoside) and gemcitabine; purine analogs such as mercaptopurine (6-niercaptopurine, 6-MP), thioguanine (6-thioguanine, TG) and pentostatin (2'-deoxycoformycin, deoxycoformycin), cladribine and fludarabine; and topoisomerase inhibitors such as amsacrine. Examples of natural products include vinca alkaloids such as vinblastine (VLB) and vincristine; taxanes such as paclitaxel (Abraxane) and docetaxel (Taxotere); epipodophyllotoxins such as etoposide and teniposide; camptothecins such as topotecan and irinotecan; antibiotics such as dactinomycin (actinomycin D), daunorubicin (daunomycin, rubidomycin), doxorubicin, bleomycin, mitomycin (mitomycin C), idarubicin, epirubicin; enzymes such as L-asparaginase; and biological response modifiers such as interferon alpha and interleukin 2. Examples of hormones and antagonists include luteinising releasing hormone agonists such as buserelin; adrenocorticosteroids such as prednisone and related preparations; progestins such as hydroxyprogesterone caproate, medroxyprogesterone acetate and megestrol acetate; estrogens such as diethylstilbestrol and ethinyl estradiol and related preparations; estrogen antagonists such as tamoxifen and anastrozole; androgens such as testosterone propionate and fluoxymesterone and related preparations; androgen antagonists such as flutamide and bicalutamide; and gonadotropin-releasing hormone analogs such as leuprolide. Examples of miscellaneous agents include thalidomide; platinum coordination complexes such as cisplatin (czs-DDP), oxaliplatin and carboplatin; anthracenediones such as mitoxantrone; substituted ureas such as hydroxyurea; methylhydrazine derivatives such as procarbazine (N-methylhydrazine, MIH); adrenocortical suppressants such as mitotane (o,p'-DDD) and aminoglutethimide; RXR agonists such as bexarotene; and tyrosine kinase inhibitors such as imatinib.

Compositions featured in the methods of the present invention can be administered in a single dose or in multiple doses. Where the administration of the antibodies by infusion, the infusion can be a single sustained dose or can be delivered by multiple infusions. Injection of the agent can be directly into the tissue at or near the site of aberrant target gene expression. Multiple injections of the agent can be made into the tissue at or near the site.

Dosage levels on the order of about 1 ug/kg to 100 mg/kg of body weight per administration are useful in the treatment of a disease. In regard to dosage, an antibody can be administered at a unit dose less than about 75 mg per kg of bodyweight, or less than about 70, 60, 50, 40, 30, 20, 10, 5, 2, 1, 0.5, 0.1, 0.05, 0.01, 0.005, 0.001, or 0.0005 mg per kg of bodyweight, and less than 200 nmol of antibody per kg of bodyweight, or less than 1500, 750, 300, 150, 75, 15, 7.5, 1.5, 0.75, 0.15, 0.075, 0.015, 0.0075, 0.0015, 0.00075, 0.00015 nmol of antibody per kg of bodyweight. The unit dose, for example, can be administered by injection (e.g., intravenous or intramuscular, intrathecally, or directly into an organ), inhalation, or a topical application.

One skilled in the art can also readily determine an appropriate dosage regimen for administering the antibody of the invention to a given subject. For example, the SPARC-binding antibody composition can be administered to the subject once, as a single injection or deposition at or near the site of SPARC expression. Compositions of the present invention can be administered daily, semi-weekly, weekly, bi-weekly, semi-monthly, monthly, bi-monthly, or at the discretion of the clinician. In some embodiments, the compositions are administered once or twice daily to a subject for a period of from about three to about twenty-eight days, more preferably from about seven to about ten days. In further embodiments, the unit dose is administered less frequently than once a day, e.g., less than every 2, 4, 8 or 30 days. In other embodiments, the unit dose is not administered with a frequency (e.g., not a regular frequency).

Where a dosage regimen comprises multiple administrations, it is understood that the effective amount of SPARC-binding antibody composition administered to the subject can include the total amount of antibody administered over the entire dosage regimen. One skilled in the art will appreciate that the exact individual dosages may be adjusted somewhat depending on a variety of factors, including the specific SPARC binding antibody composition being administered, the time of administration, the route of administration, the nature of the formulation, the rate of excretion, the particular disorder being treated, the severity of the disorder, the pharmacodynamics of the oligonucleotide agent, and the age, sex, weight, and general health of the patient. Wide variations in the necessary dosage level are to be expected in view of the differing efficiencies of the various routes of administration.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable. Following successful treatment, it may be desirable to have the patient undergo maintenance therapy to prevent the recurrence of the disease state. The concentration of the antibody composition is an amount sufficient to be effective in treating or preventing a disorder or to regulate a physiological condition in humans. The concentration or amount of antibody administered will depend on the parameters determined for the agent and the method of administration.

Certain factors may influence the dosage required to effectively treat a subject, including but not limited to the severity of the disease or disorder, previous treatments, the general health and/or age of the subject, and other diseases present. It will also be appreciated that the effective dosage of the antibody used for treatment may increase or decrease over the course of a particular treatment. Changes in dosage may result and become apparent from the results of diagnostic assays. For example, the subject can be monitored after administering an antibody composition. Based on information from the monitoring, an additional amount of the antibody composition can be administered. Persons of ordinary skill can easily determine optimum dosages, dosing methodologies and repetition rates.

Example 1

This Example demonstrates the preparation of a series of antibodies capable of binding to human SPARC.

Twelve mouse-derived anti-human SPARC antibodies were commercially generated using a conventional hybridoma approach using mouse strain RBF/DnJ.

Figure 1:
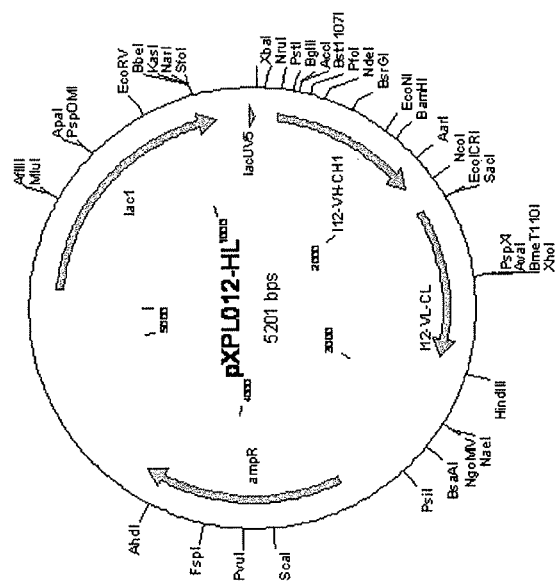

A pASK84 expression vector (FIG. 1) was used to express the Fab regions of the resulting antibodies, designated Imm1-Imm-12. The Fab regions were targeted to the periplasm where they were collected and subsequently purified via activity chromatography on a protein A sepharose column. Identity was verified by Western blot and SPARC binding activity was verified by ELISA.

Imm-13 and 14 are fully human anti-human SPARC antibodies which were generated using a human phage display library. SPARC was panned against the commercial human Fab phage display library HuFabL® (Creative Biolabs, Shirley, N.Y.). Two Fab sequences of interest were identified: Fab6 (SEQ ID NO 15) and Fab16 (SEQ ID NO 16), as shown in FIG. 2. SPARC binding activity was verified by ELISA for these two Fab molecules.

Figure 3:
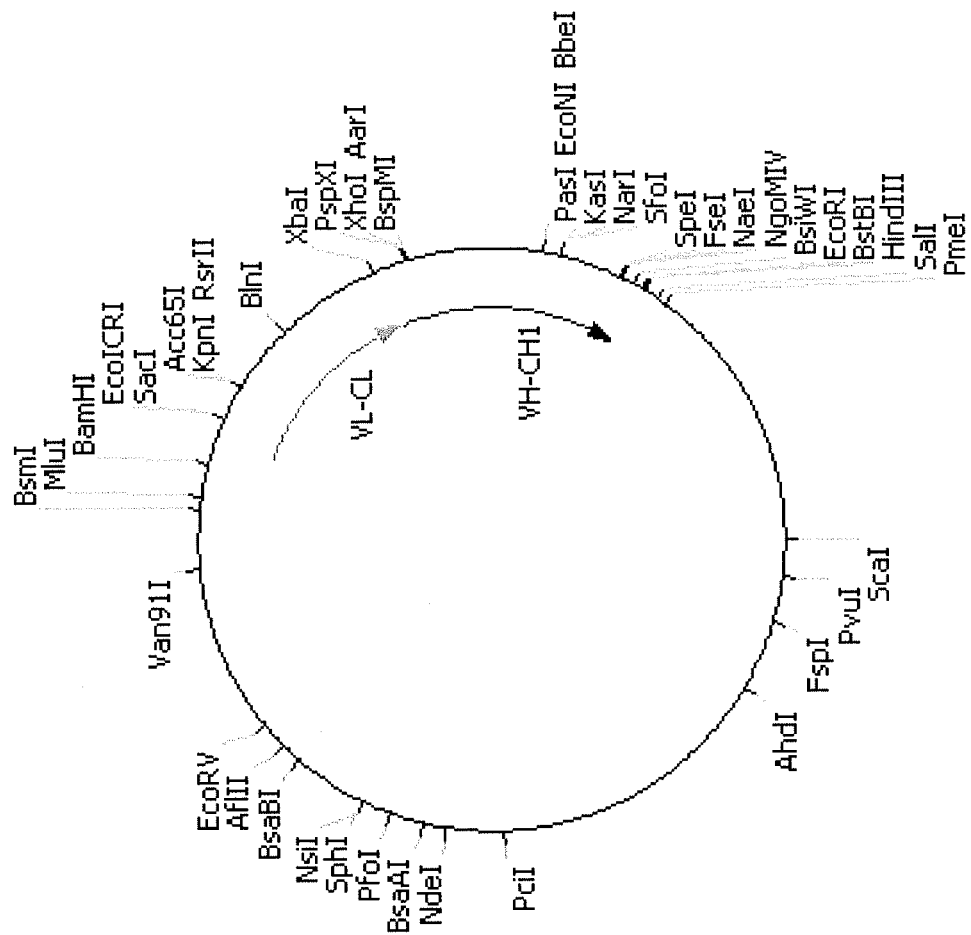

These Fab regions were cloned into the pBAD vector (FIG. 3) and were expressed and purified in bacteria. The Fab proteins expressed by the pBAD vector were isolated from the periplasmic fraction of lysed bacteria, with sequences provided at FIG. 4. The identities of the Fab regions obtained from the periplasmic fraction were verified by SDS page. The Fab proteins were purified to homogeneity via activity chromatography on a protein A sepharose column.

In order to create fully human anti-SPARC antibodies, the genes for Fab6 and Fab16 were cloned and expressed via the pcDNA3002Neo Vector (Invitrogen, Carlsbad, Calif.) (FIG. 21). The resultant antibodies were purified and their identities were verified by gel electrophoresis and N-terminal analysis.

The fully human antibody created from Fab6 was designated Imm-13 and the fully human antibody created from Fab16 was designated Imm-14.

After they were generated according to the foregoing methods, Imm-1 through Imm14 antibodies were characterized according to isotype by utilizing a commercial mouse isotyping test kit (AbD Serotec, Raleigh, N.C.). The results are presented in Table 1.

TABLE 1

| Clone Number | Abraxis Name | Isotype |
|---|---|---|
| 16 | Imm-1 | IgG1 (κ) |
| 38 | Imm-2 | IgG1, 2b (κ) |
| 39 | Imm-3 | IgG1, 2b (κ) |
| 43 | Imm-4 | IgG1 (κ) |
| 47 | Imm-5 | IgG2a (κ) |
| 49 | Imm-6 | IgG1 (κ) |
| 55 | Imm-7 | IgG2a (κ) |
| 58 | Imm-8 | IgG2b (κ) |
| 62 | Imm-9 | IgG1 (κ) |
| 66 | Imm-10 | IgG1 (κ) |
| 70 | Imm-11 | IgG1 (κ) |
| 71 | Imm-12 | IgG1 (κ) |
| F6 | Imm-13 | IgG1 (κ) |
| F16 | Imm-14 | IgG1 (κ) |

Figure 5:
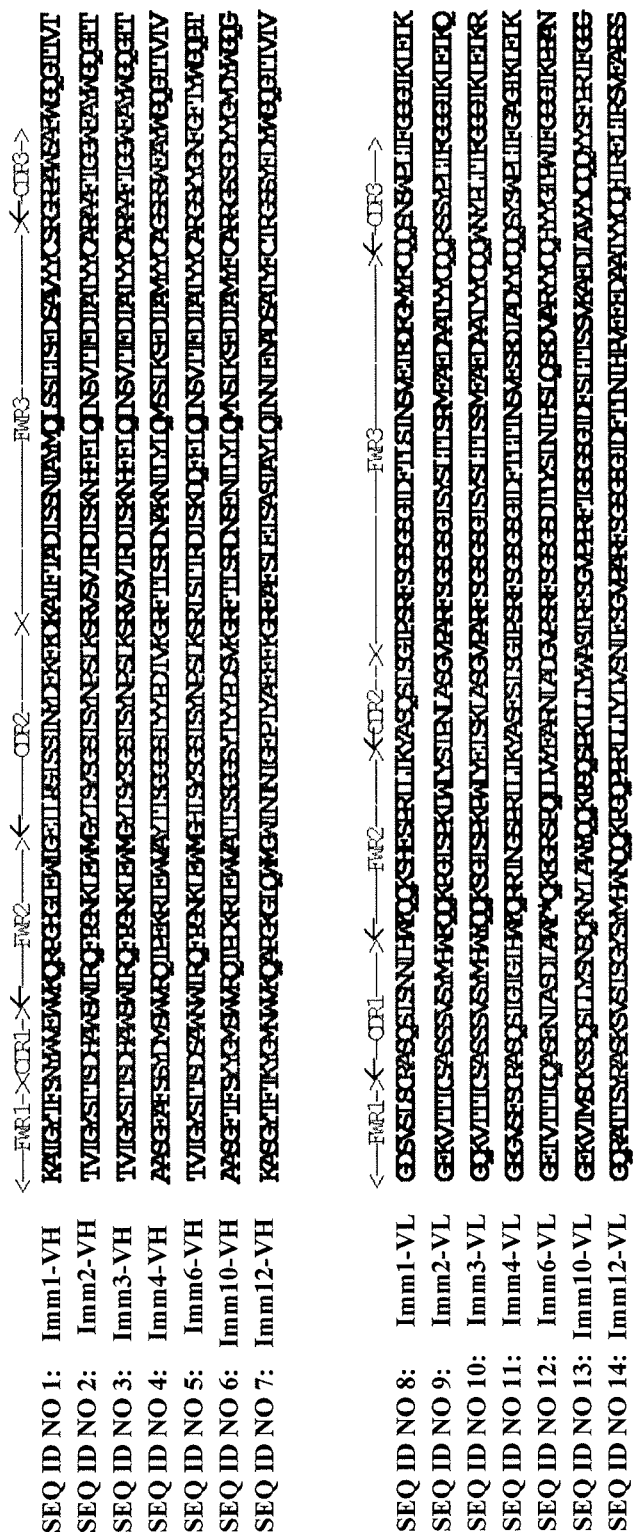

The sequences for the variable complimentary determining regions for selected Imm-series antibodies, including Imm-2 and Imm-3, are presented in FIG. 5. The clones in Table 1, Imm-1 through Imm-14, will be deposited at a suitable depository, such as the ATTC.

Example 2

This Example demonstrates the use of ELISA assays to characterize the SPARC binding of the Imm-series antibodies.

Figure 6:
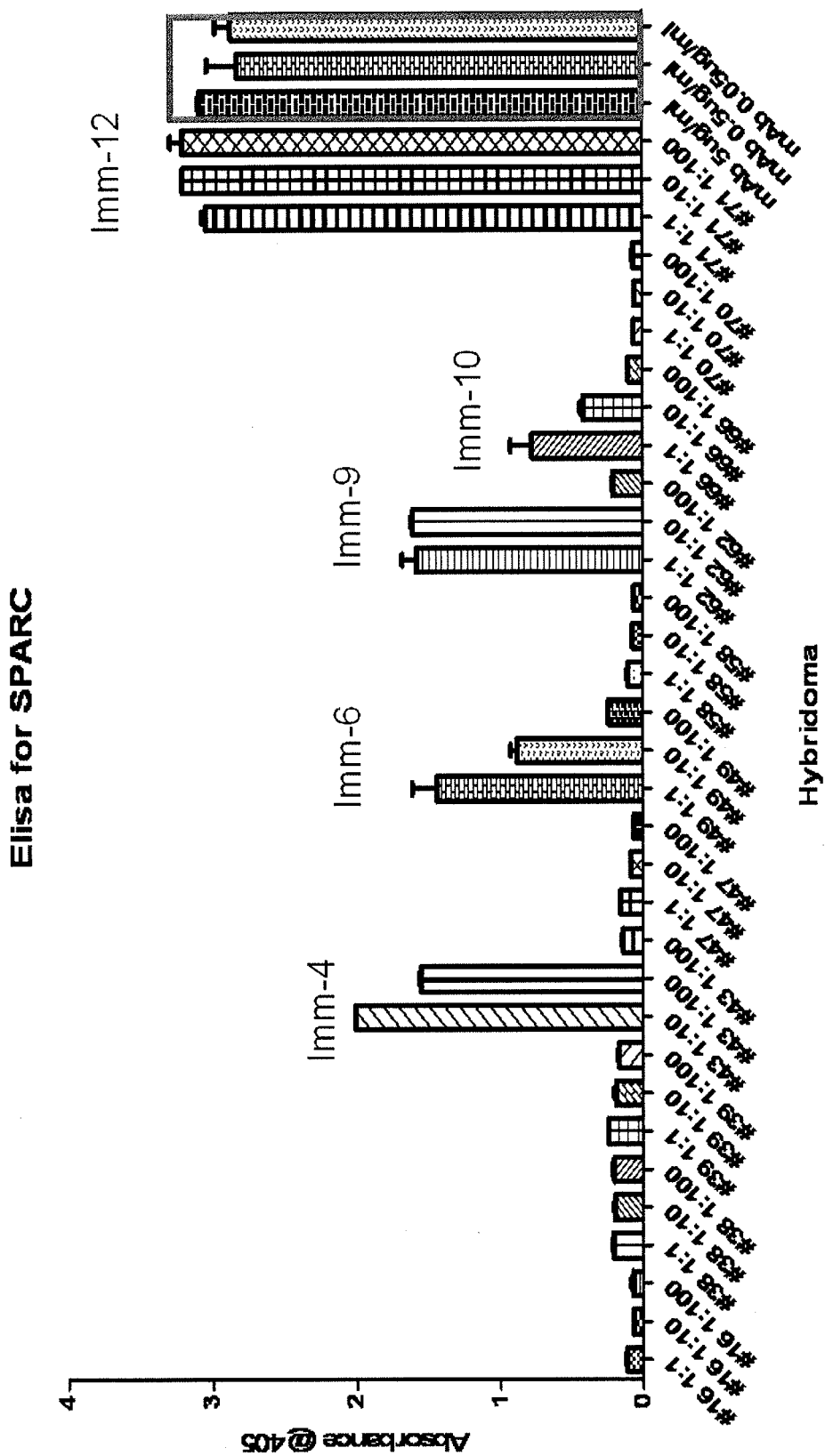
Figure 7:
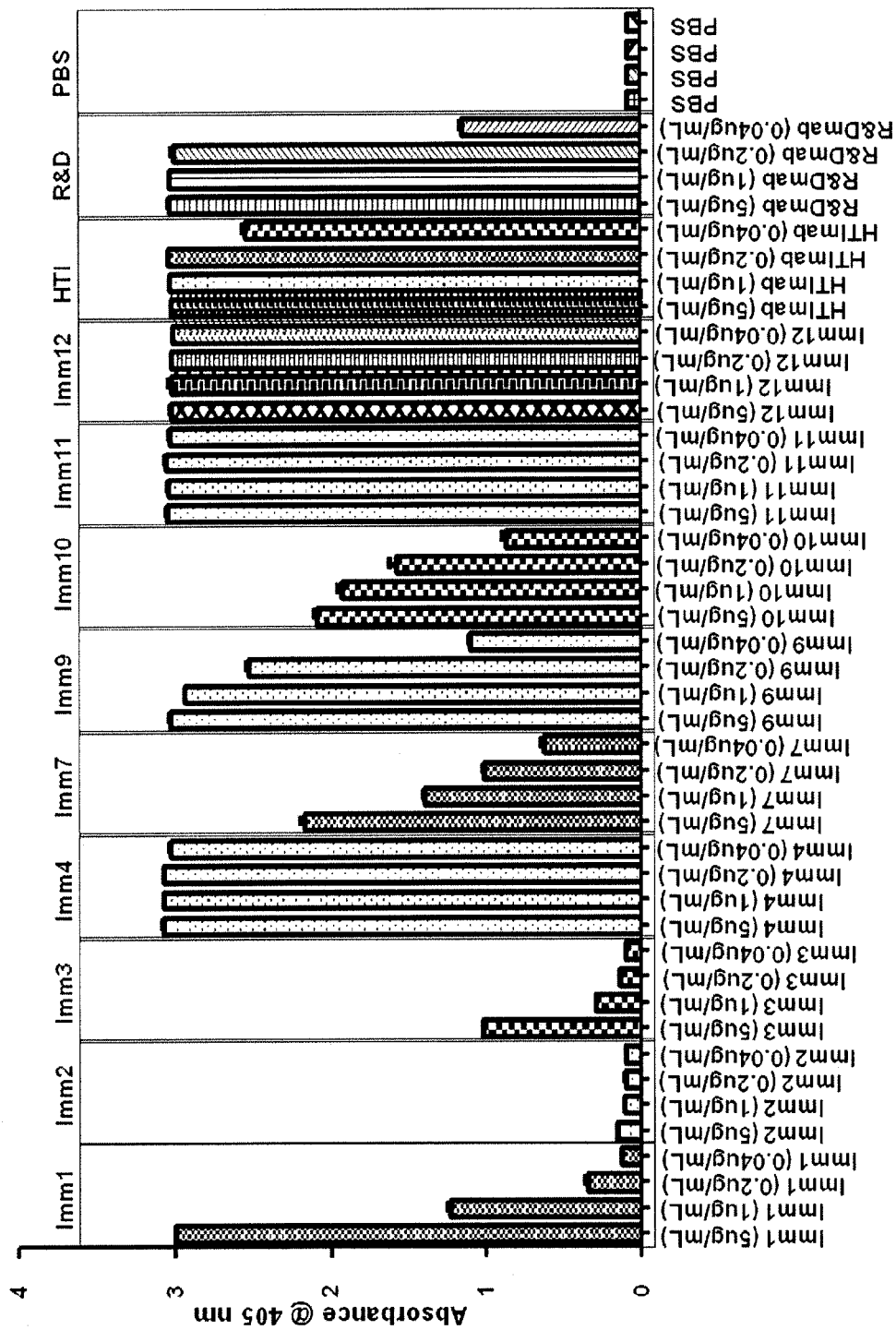
Figure 8:
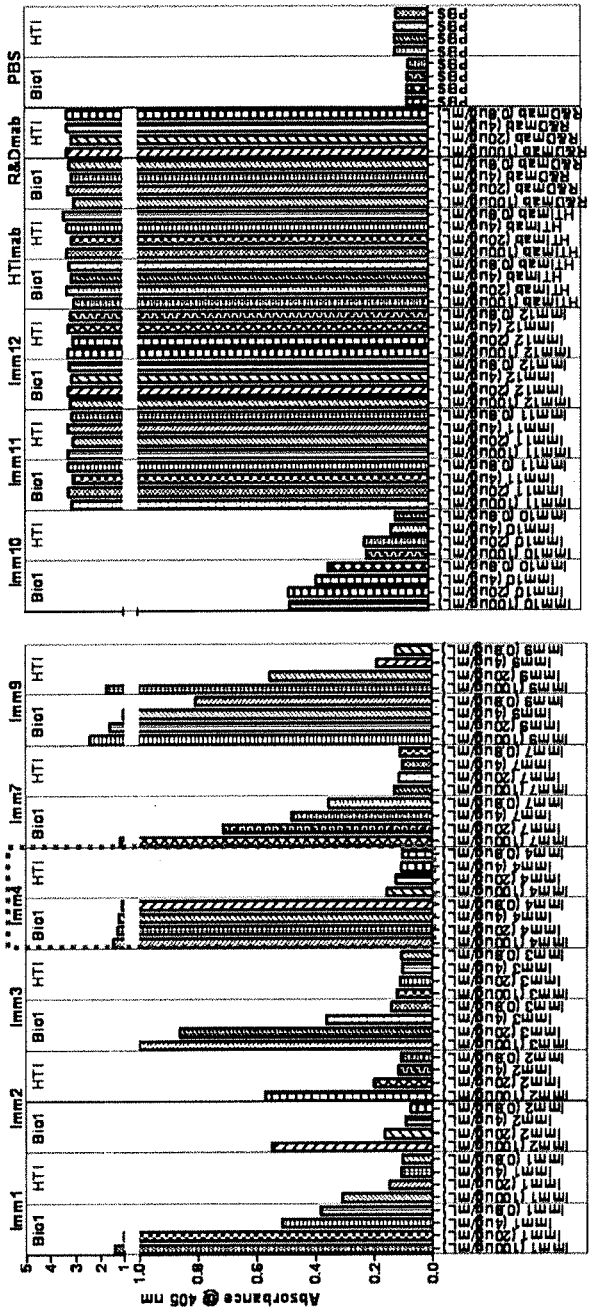

The ability of Imm-1 through Imm-12 (the mouse-derived anti-human SPARC antibodies) to bind recombinant human SPARC (Bio1-SPARC) was characterized by multiple ELISA assays performed at various stages of purification. FIG. 6 presents the results of an ELISA assay performed on a serial dilution (1:1, 1:10, and 1:100) of antibody supernatants prior to purification. In this assay, Imm-4, Imm-6, Imm-9, Imm-10 and Imm-12 exhibited the highest Bio1-SPARC binding, with Imm-12 exhibiting the highest binding overall. Another ELISA assay was performed with the purified antibodies (FIG. 7) at concentrations of 0.04 µg/mL, 0.2 µg/mL, 1 µg/mL, and 5 µg/mL. The binding of the purified antibodies was generally improved over the unpurified supernatants. In this assay, Imm-4, Imm-9, Imm-11 and Imm-12 exhibited the highest Bio1-SPARC binding. An additional ELISA was performed to compare the binding of the mouse derived Imm-series antibodies to two different varieties of SPARC: Bio1-SPARC, and human platelet SPARC (HTI-SPARC) (FIG. 8). In this assay, Imm-4 and Imm-9 were both found to bind Bio1-SPARC significantly better than HTI-SPARC. Imm-11 and Imm-12 bind both varieties of human SPARC equally well.

Figure 9:
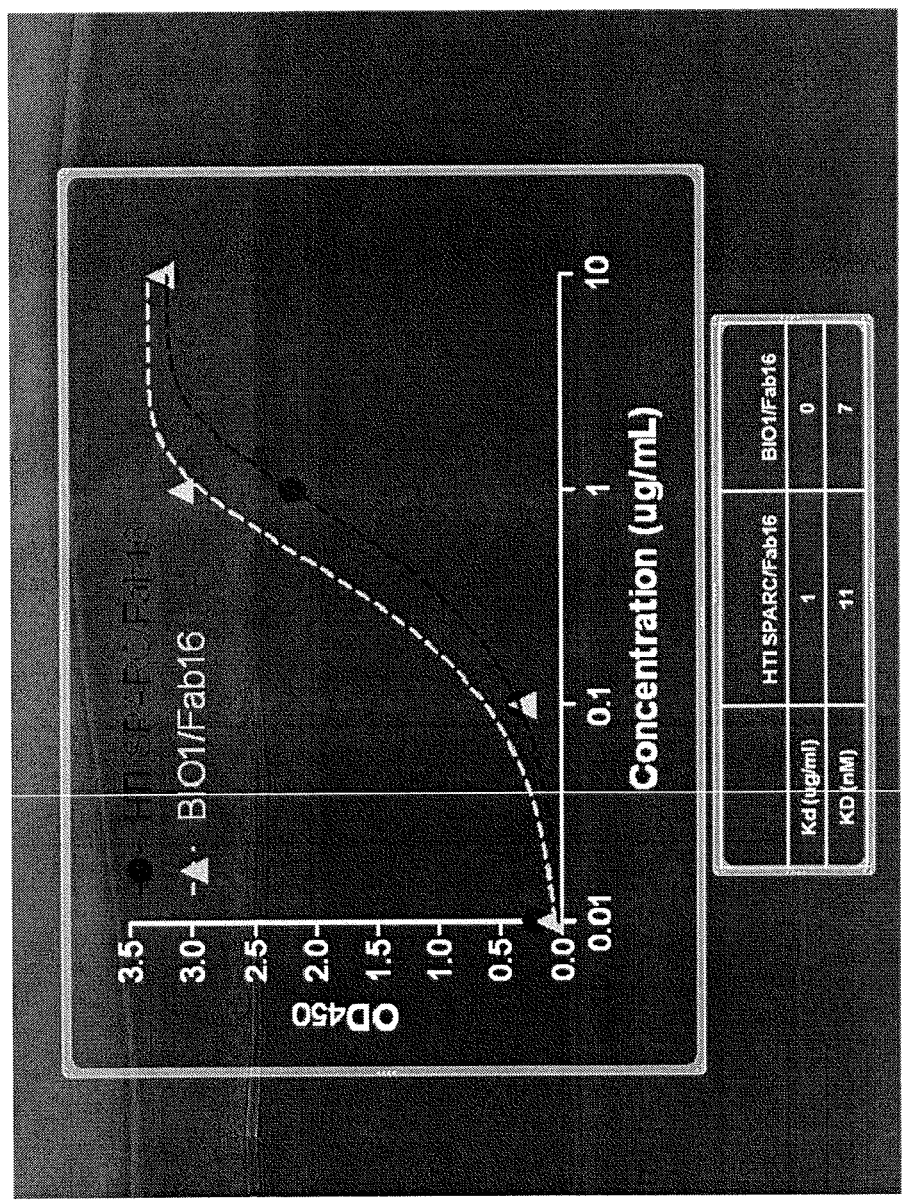
Figure 10:
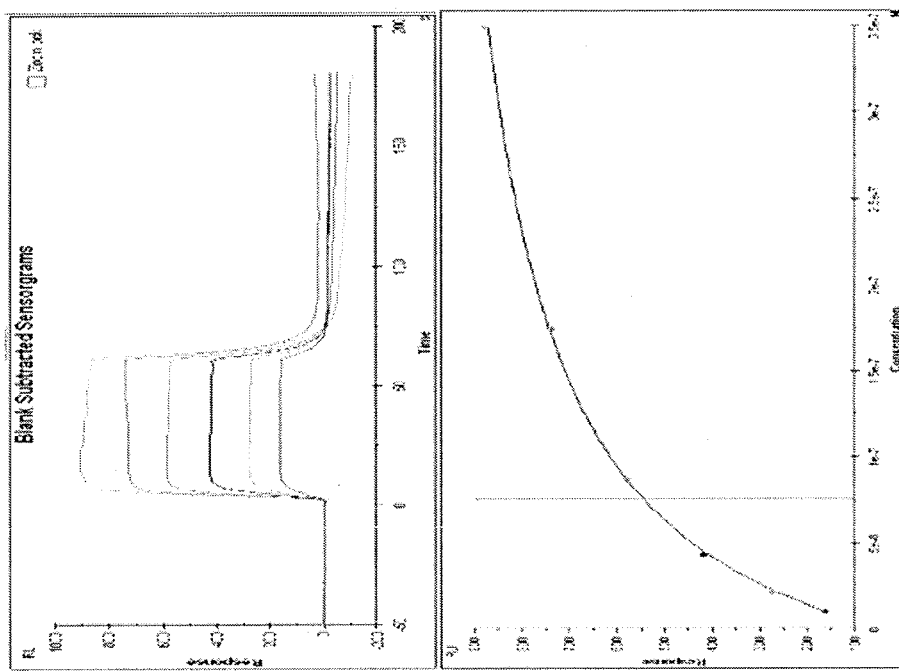
FIG. 10 is a sensorgram prepared using surface plasmon resonance of Fab16 (SEQ ID NO: 20) binding to human HTI SPARC.
Figure 11:
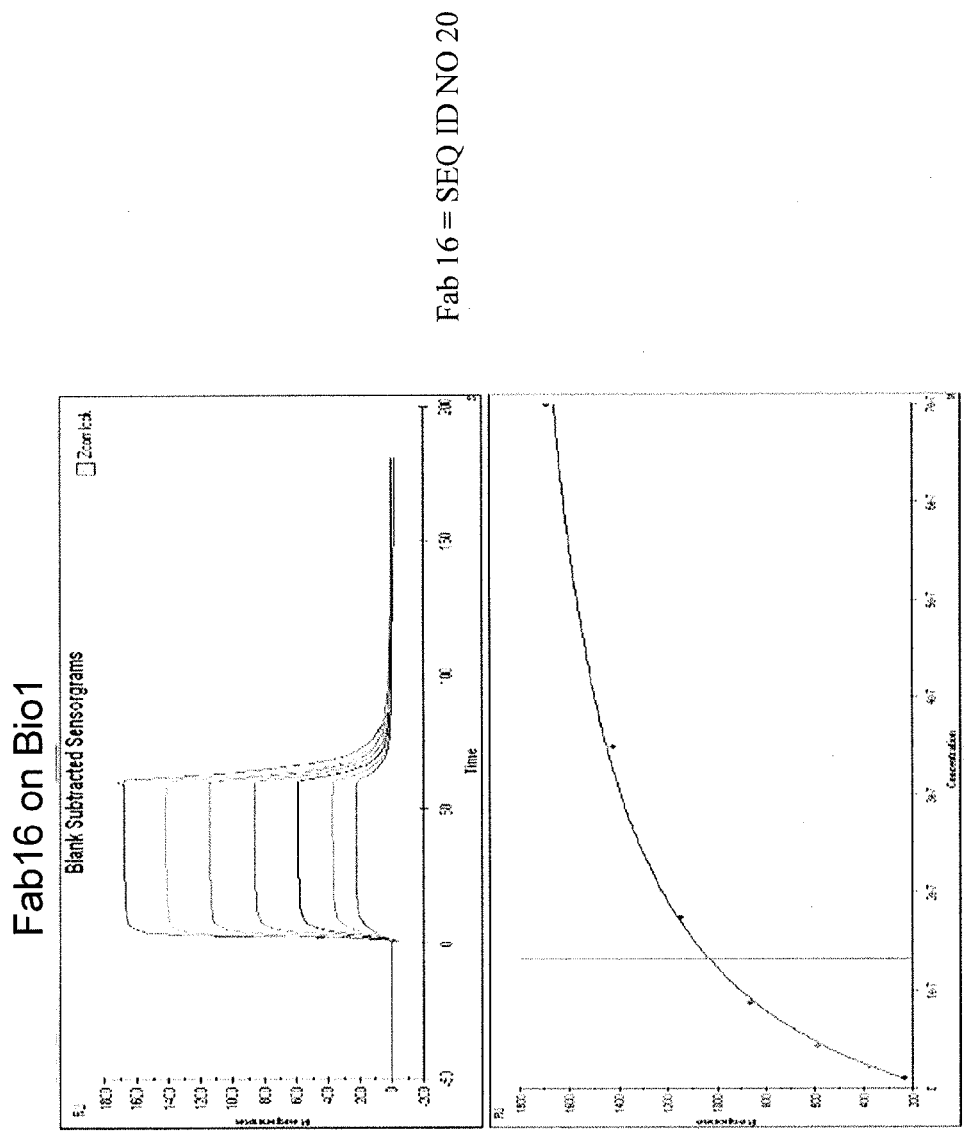
FIG. 11 is a sensorgram prepared using surface plasmon resonance of Fab16 (SEQ ID NO: 20) binding to human BIO1 SPARC.

ELISA assays were also used to characterize the SPARC binding of the fully human anti-SPARC antibodies, Imm-13 and Imm-14. For example, according to a protein ELISA assay (FIG. 9), Fab16 (the Fab region of Imm-14) binds HTI-SPARC with a $K_D$ of 11 nM and binds Bio1-SPARC with a $K_D$ of 7 nM. Surface plasmon resonance binding assays, performed on the Biacore 3000® (GE/Biacore International AB, Uppsala, Sweden), tested the binding of Fab16 to both varieties of SPARC immobilized on a sensorchip (FIGS. 10 and 11). These assays resulted in $K_D$ values of 76.2 nM for HTI SPARC and 132 nM for Bio1-SPARC.

An ELISA assay was also performed to directly compare the SPARC binding capabilities of selected mouse-derived anti human SPARC antibodies, Imm-11 and Imm-12, to the fully human Imm-13 and Imm-14, the results of which are presented in FIG. 24. The results indicate that Imm-13 has a higher affinity for SPARC than both of the mouse derived antibodies, while Imm-14 has a lower affinity.

This example demonstrates that certain of the Imm series antibodies bind, in vitro, to both recombinant human SPARC and human platelet SPARC in binding assays.

Example 3

This example demonstrates the analysis of the epitopes to which the Imm-series antibodies bind.

Western blotting was used to determine whether the Imm-series antibodies bind to linear or conformational epitopes. In this analysis, SPARC protein was run on a polyacrylamide gel in the presence of SDS. Accordingly, the SPARC protein on the gel was in its denatured form. The Imm-series antibodies were used as primary antibodies and were then probed with goat anti-mouse IgG. BSA was used as a negative control. The results of the assay, shown at FIG. 13, show binding of Imm-11 and Imm-12 to SPARC. Binding to the other Imm series antibodies was not detected by this assay.

Further epitope mapping analyses using phage display. In brief, the mAbs were exposed to phage display library, washed to remove nonspecific binders, and the bound phages eluted and sequenced. The peptide sequences provided at FIGS. 15-16 confirm that several of the Imm-series antibodies were found to recognize different epitopes with some spanning multiple sequence positions when the phage sequences were aligned against SPARC protein sequence using Clone Manager program (FIG. 14).

These results show that Imm-11 and Imm-12 bind SPARC based on linear, or primary, epitopes, while the remaining Imm-series antibodies bind SPARC at epitopes of higher order structure rather than on the primary amino acid sequence alone.

Example 4

This example demonstrates the ability of Imm-2 and Imm-3 to localize at a tumor site in an in vivo tumor model.

Nude mice implanted with subcutaneous HT29 colon xenografts were treated with Imm series antibodies labeled with labeled with Alexa 680 fluorescent dye at dose of 200 ug/mouse. The labeled Imm antibodies were formulated in saline and administered intravenously on day 1. The fluorescent signal was followed in these mice over the course of 36 days.

FIG. 17 depicts the results of this study. Imm-2 and Imm-3 show greater tumor localization than other evaluated antibodies. Tumor specific localization was detectable as early as one day after initial administration and progressively increased until day 36. FIGS. 18 and 19 provide exemplary display of Imm-2's ability to visualize tumors at days 18 and 28 respectively.

Despite strong SPARC binding in ELISA assays, Imm-4, Imm-9, Imm-11, Imm-12 and Imm-13 were not able to localize to the tumor in vivo.

These data indicate that SPARC epitopes are generally not available in vivo. Accordingly Imm-2 and Imm-3, which are

Example 5

This Example discusses results of in vivo assay examining the effect of certain Imm-series antibodies on survival in nude mice challenged with LL/2 Lewis Lung Carcinoma. The animals in the study were administered either Imm-2, Imm-12, or Imm-14. A negative control group was administered mIgG. The antibodies were formulated in PBS and were administered in at dose of 200 ug/mouse, 2×wkly, for four weeks. The survival of the animals was then recorded over twenty days.

A higher percentage of animals treated with Imm-2 survived at the various time points than did animals treated with Imm-12 or Imm-14. FIG. 20 depicts the results of the study.

These results indicate that Imm-2 may be useful in treating cancer.

Example 6

This example illustrates the use of the antibodies of the present invention to diagnose a proliferative disease.

A suitable quantity of Imm-2 and/or Imm-3 is prepared in accordance with the methods described above or via other methods known in the art. The antibodies are conjugated to a diagnostic agent suitable for medical imaging, such as a radionuclide, using a conjugation method known in the art.

The composition is applied to tissue samples taken from a test cohort of patients suffering from a proliferative disease associated with the overexpression of SPARC, e.g. breast cancer. The composition is likewise applied to tissue samples taken from a negative control cohort, not suffering from a proliferative disease.

The use of appropriate medical imaging techniques on the test cohort samples indicates the presence of disease, while the same techniques applied to the control cohort samples indicate the absence of disease.

The results will show that the antibodies of the present invention are useful in diagnosing proliferative diseases.

Example 7

This example illustrates the use of the antibodies of the present invention to treat a proliferative disease in a mouse tumor model.

A suitable quantity of Imm-2 and/or Imm-3 is prepared in accordance with the methods described above or via other methods known in the art. The antibodies are conjugated to a chemotherapeutic agent, such as Doxil, using an appropriate conjugation method known in the art. The conjugate is formulated in an aqueous composition.

The composition is administered intravenously, in one or more doses, to a test cohort of mice suffering from a proliferative disease associated with the overexpression of SPARC, e.g. a breast cancer model. A control cohort, not suffering from a proliferative disease is administered the identical composition intravenously, according to a corresponding dosage regimen.

Pathological analysis of tumor samples and/or mouse survival indicate that mortality and/or morbidity are improved in the test cohort over the control cohort.

The results will show that the antibodies of the present invention are useful in treating proliferative diseases.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A composition comprising a SPARC binding antibody, wherein the SPARC binding antibody comprises Imm-2, Imm-3, or a combination thereof.

2. The composition of claim 1 wherein the SPARC binding antibody comprises Imm-2.

3. The composition of claim 1 wherein the SPARC binding antibody comprises Imm-3.

4. The composition of claim 1 wherein the SPARC binding antibody comprises both Imm-2 and Imm-3.

5. The composition of claim 1, further comprising an active agent, wherein the active agent is conjugated to the SPARC binding antibody.

6. The composition of claim 5, wherein the active agent comprises a therapeutic agent or a diagnostic agent.

7. The composition of claim 6, wherein the therapeutic agent or diagnostic agent is a therapeutic agent selected from the group consisting of tyrosine kinase inhibitors, kinase inhibitors, biologically active agents, biological molecules, radionuclides, adriamycin, ansamycin antibiotics, asparaginase, bleomycin, busulphan, cisplatin, carboplatin, carmustine, capecitabine, chlorambucil, cytarabine, cyclophosphamide, camptothecin, dacarbazine, dactinomycin, daunorubicin, dexrazoxane, docetaxel, doxorubicin, etoposide, epothilones, floxuridine, fludarabine, fluorouracil, gemcitabine, hydroxyurea, idarubicin, ifosfamide, irinotecan, lomustine, mechlorethamine, mercaptopurine, meplhalan, methotrexate, rapamycin (sirolimus), mitomycin, mitotane, mitoxantrone, nitrosurea, paclitaxel, pamidronate, pentostatin, plicamycin, procarbazine, rituximab, streptozocin, teniposide, thioguanine, thiotepa, taxanes, vinblastine, vincristine, vinorelbine, taxol, combretastatins, discodermolides, transplatinum, anti-vascular endothelial growth factor compounds ("anti-VEGFs"), anti-epidermal growth factor receptor compounds "anti-EGFRs"), 5-fluorouracil and derivatives, radionuclides, polypeptide toxins, apoptosis inducers, therapy sensitizers, enzyme or active fragment thereof, and combinations thereof.

8. The composition of claim 6, wherein the therapeutic agent or diagnostic agent is a therapeutic agent comprising an antibody or antibody fragment.

9. The composition of claim 8, wherein said antibody or antibody fragment is a Fc fragment of IgG, or IgA, or IgD, or IgE, or IgM.

10. The composition of claim 8, wherein said antibody or antibody fragment mediates one or more of complement activation, cell mediated cytotoxicity or opsonization, or mast cell activation, or other immune response.

11. The composition of claim 6, wherein the therapeutic agent or diagnostic agent is a diagnostic agent selected from the group consisting of flurochromes, radioactive agents, MRI contrast agents, X-ray contrast agents, ultrasound contrast agents, and PET contrast agents.

12. The composition of claim 1, wherein the composition is contained in a liposome.

13. The composition of claim 1, wherein the composition is contained in an albumin nanoparticle.

14. The composition of claim 1, wherein the composition further comprises a suitable pharmaceutical carrier.

15. The composition of claim 1, wherein said composition is administered to a patient via i.v., topically, via injection, via inhalation, intranasally, rectally or orally.

* * * * *